United States Patent [19]
Cooper et al.

[11] Patent Number: 5,925,648
[45] Date of Patent: Jul. 20, 1999

[54] TRICYCLIC N-CYANOIMINES USEFUL AS INHIBITORS OF A FARNESYL-PROTEIN TRANSFERASE

[75] Inventors: Alan B. Cooper, West Caldwell; James J-S Wang, Westfield; Raymond G. Lovey, West Caldwell; Jagdish A. Desai, Spotswood; Anil K. Saksena, Upper Montclair; Viyyoor M. Girijavallabhan, Parsippany; Ronald J. Doll, Maplewood, all of N.J.

[73] Assignee: Schering Corporation, Kenilworth, N.J.

[21] Appl. No.: 08/902,372

[22] Filed: Jul. 29, 1997

[51] Int. Cl.⁶ .................. A61K 31/44; C07D 401/04
[52] U.S. Cl. .................. 514/290; 514/232.8; 514/255; 544/126; 544/361; 546/93
[58] Field of Search .................. 514/255, 290, 514/232.8; 544/361, 126; 546/93

[56] References Cited

U.S. PATENT DOCUMENTS

| | | | |
|---|---|---|---|
| 3,975,530 | 8/1976 | Durant et al. | 514/365 |
| 5,089,496 | 2/1992 | Piwinski et al. | 514/253 |
| 5,192,537 | 3/1993 | Osband | 424/85.2 |

FOREIGN PATENT DOCUMENTS

| | | |
|---|---|---|
| 0 270 818 A1 | 6/1988 | European Pat. Off. . |
| 0341 860 | 11/1989 | European Pat. Off. . |
| WO 95/10515 | 4/1995 | WIPO . |
| WO 95/10516 | 4/1995 | WIPO . |

OTHER PUBLICATIONS

Cecil Textbook of Medicine, edited by Wyngaarden, J.B. et al., 19th edition, W.B. Saunders Co., pp. 827–831 and 2304–2305, 1992.

*Primary Examiner*—Yogendra N. Gupta
*Attorney, Agent, or Firm*—Joseph T. Majka

[57] ABSTRACT

Novel tricyclic N-cyanoimine compounds and pharmaceutical compositions of formula (1.0)

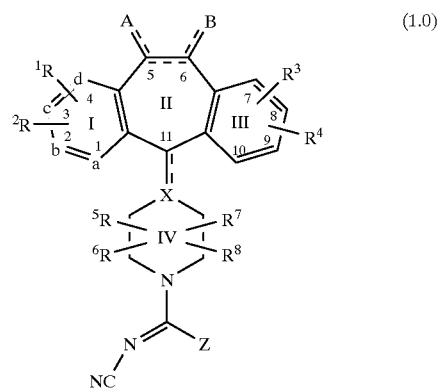

or a pharmaceutically acceptable salt or solvate thereof, wherein a, b, c, d, $R^1$-$R^8$, X and Z are defined herein. Such compounds are inhibitors of the enzyme, farnesyl protein transferase. The compounds are useful for inhibiting Ras function and therefore inhibiting the abnormal growth of cells, in a mammals such as a human.

13 Claims, No Drawings

TRICYCLIC N-CYANOIMINES USEFUL AS INHIBITORS OF A FARNESYL-PROTEIN TRANSFERASE

BACKGROUND

Patent application WO 95/00497 published Jan. 5, 1995 under the Patent Cooperation Treaty (PCT) describes compounds which inhibit the enzyme, farnesyl-protein transferase (FTase) and the farnesylation of the oncogene protein Ras. Oncogenes frequently encode protein components of signal transduction pathways which lead to stimulation of cell growth and mitogenesis. Oncogene expression in cultured cells leads to cellular transformation, characterized by the ability of cells to grow in soft agar and the growth of cells as dense foci lacking the contact inhibition exhibited by non-transformed cells. Mutation and/or overexpression of certain oncogenes is frequently associated with human cancer.

To acquire transforming potential, the precursor of the Ras oncoprotein must undergo farnesylation of the cysteine residue located in a carboxyl-terminal tetrapeptide. Inhibitors of the enzyme that catalyzes this modification, farnesyl protein transferase, have therefore been suggested as anticancer agents for tumors in which Ras contributes to transformation. Mutated, oncogenic forms of Ras are frequently found in many human cancers, most notably in more than 50% of colon and pancreatic carcinomas (Kohl et al., Science, Vol. 260, 1834 to 1837, 1993).

In view of the current interest in inhibitors of farnesyl protein transferase, a welcome contribution to the art would be additional compounds useful for the inhibition of farnesyl protein transferase. Such a contribution is provided by this invention.

SUMMARY OF THE INVENTION

Inhibition of farnesyl protein transferase by tricyclic compounds of this invention has not been reported previously. Thus, this invention provides a method for inhibiting farnesyl protein transferase using tricyclic compounds of this invention which: (i) potently inhibit farnesyl protein transferase, but not geranylgeranyl protein transferase I, in vitro; (ii) block the phenotypic change induced by a form of transforming Ras which is a farnesyl acceptor but not by a form of transforming Ras engineered to be a geranylgeranyl acceptor; (iii) block intracellular processing of Ras which is a farnesyl acceptor but not of Ras engineered to be a geranylgeranyl acceptor; and (iv) block abnormal cell growth in culture induced by transforming Ras. Several compounds of this invention have been demonstrated to have anti-tumor activity in animal models.

This invention provides a method for inhibiting the abnormal growth of cells, including transformed cells, by administering an effective amount of a compound of this invention. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; and (3) benign and malignant cells of other proliferative diseases in which aberrant Ras activation occurs.

Compounds useful in the claimed methods are represented by Formula 1.0:

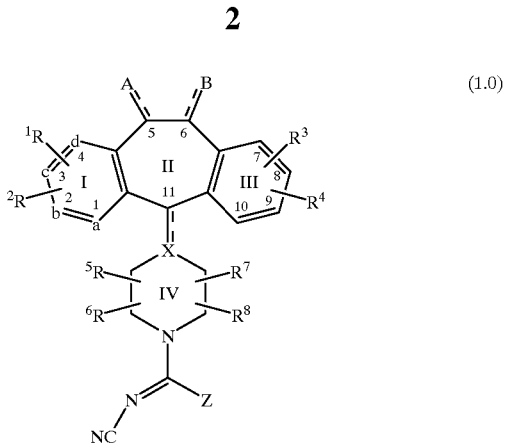

or a pharmaceutically acceptable salt or solvate thereof, wherein:

one of a, b, c and d represents N or $NR^9$ wherein $R^9$ is $O^-$, $-CH_3$ or $-(CH_2)_nCO_2H$ wherein n is 1 to 3, and the remaining a, b, c and d groups represent $CR^1$ or $CR^2$; or each of a, b, c, and d are independently selected from $CR^1$ or $CR^2$; each $R^1$ and each $R^2$ is independently selected from H, halo, $-CF_3$, $-OR^{10}$ (e.g., $-OCH_3$), $-COR^{10}$, $-SR^{10}$ (e.g., $-SCH_3$ and $-SCH_2C_6H_5$), $-S(O)_tR^{11}$ (wherein t is 0, 1 or 2, e.g., $-SOCH_3$ and $-SO_2CH_3$), $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR_{10}$, $-CONHCH_2CH_2OH$, $-NR^{10}COOR^{11}$, $-SR^{11}C(O)OR^{11}$ (e.g., $-SCH_2CO_2CH_3$), $-SR^{11}N(R^{75})_2$ wherein each $R^{75}$ is independently selected from H and $-C(O)OR^{11}$ (e.g., $-S(CH_2)_2NHC(O)O$—t-butyl and $-S(CH_2)_2NH_2$), benzotriazol-1-yloxy, tetrazol-5-ylthio, or substituted tetrazol-5-ylthio (e.g., alkyl substituted tetrazol5-ylthio such as 1-methyl-tetrazol-5-ylthio), alkynyl, alkenyl or alkyl, said alkyl or alkenyl group optionally being substituted with halo, $-OR^{10}$ or $-CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5-C_7$ fused ring to the benzene ring (Ring III);

$R^5$, $R^6$, $R^7$ and $R^8$ each independently represents H, $-CF_3$, $-COR^{10}$, alkyl or aryl, said alkyl or aryl optionally being substituted with $-OR^{10}$, $-SR^{10}$, $-S(O)_tR^{11}$, $-NR^{10}COOR^{11}$, $-N(R^{10})_2$, $-NO_2$, $-COR^{10}$, $-OCOR^{10}$, $-OCO_2R^{11}$, $-CO_2R^{10}$, $OPO_3R^{10}$ or one of $R^5$, $R^6$, $R^7$ and $R^8$ can be taken in combination with $R^{40}$ as defined below to represent $-(CH_2)_r-$ wherein r is 1 to 4 which can be substituted with lower alkyl, lower alkoxy, $-CF_3$ or aryl, or $R^5$ is combined with $R^6$ to represent $=O$ or $=S$ and/or $R^7$ is combined with $R^8$ to represent $=O$ or $=S$;

$R^{10}$ and $R^{12}$ independently represent H, alkyl, cycloalkyl, cycloalkylalkyl, heteroaryl, aryl, aralkyl or $-NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl, cycloalkylalkyl, alkenyl and alkynyl;

$R^{11}$ represents alkyl or aryl;

X represents N, CH or C, such that when X is N or CH, there is a single bond to carbon atom 11 as represented by the solid line; or when X is C, there is a double bond to carbon atom 11, as represented by the solid and dotted lines;

the dotted line between carbon atoms 5 and 6 represents an optional double bond, such that when a double bond is present, A and B independently represent $-NO_2$, $-R^{10}$, halo, $-OR^{11}$, $-OCO_2R^{11}$ or $-OC(O)R^{10}$, and when no double bond is present between carbon atoms 5 and 6, A and B each independently represent $H_2$, —$(OR^{11})_2$, H and halo, dihalo, alkyl and H, (alkyl)$_2$, —H and —OC(O)$R^{10}$, H and —$OR^{10}$, oxy, aryl and H, =NOR$^{10}$ or —O—(CH$_2)_p$—O— wherein p is 2, 3 or 4; and Z represents alkyl, aryl, aralkyl, heteroalkyl, heteroaryl, heteroarylalkyl, heterocycloalkyl, heterocycloalkylalkyl, —$OR^{40}$, —$SR^{40}$, —$CR^{40}R^{42}$ or —$NR^{40}R^{42}$ wherein $R^{40}$ and $R^{42}$ are defined hereinbefore.

Preferably in compound (1.0), there is a single bond at carbon atom 11, X is carbon, positions 3, 8 and 10 are substituted on the ring, preferably with halo; and Z is —$NHR^{40}$, preferably where $R^{40}$ is heteroarylalkyl, more preferably 3 or 4-methyl pyridyl N-oxide.

In another embodiment, the present invention is directed toward a pharmaceutical composition for inhibiting the abnormal growth of cells comprising an effective amount of compound (1.0) in combination with a pharmaceutically acceptable carrier.

In another embodiment, the present invention is directed toward a method for inhibiting the abnormal growth of cells, including transformed cells, comprising administering an effective amount of compound (1.0) to a mammal (e.g., a human) in need of such treatment. Abnormal growth of cells refers to cell growth independent of normal regulatory mechanisms (e.g., loss of contact inhibition). This includes the abnormal growth of: (1) tumor cells (tumors) expressing an activated Ras oncogene; (2) tumor cells in which the Ras protein is activated as a result of oncogenic mutation in another gene; (3) benign and malignant cells of other proliferative diseases in which aberrant Ras activation occurs, and (4) benign or malignant cells that are activated by mechanisms other than the Ras protein. Without wishing to be bound by theory, it is believed that these compounds may function either through the inhibition of G-protein function, such as ras p21, by blocking G-protein isoprenylation, thus making them useful in the treatment of proliferative diseases such as tumor growth and cancer, or through inhibition of ras farnesyl protein transferase, thus making them useful for their antiproliferative activity against ras transformed cells.

The cells to be inhibited can be tumor cells expressing an activated ras oncogene. For example, the types of cells that may be inhibited include pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells. Also, the inhibition of the abnormal growth of cells by the treatment with compound (1.0) may be by inhibiting ras farnesyl protein transferase. The inhibition may be of tumor cells wherein the Ras protein is activated as a result of oncogenic mutation in genes other than the Ras gene. Alternatively, compounds (1.0) may inhibit tumor cells activated by a protein other than the Ras protein.

This invention also provides a method for inhibiting tumor growth by administering an effective amount of compound (1.0) to a mammal (e.g., a human) in need of such treatment. In particular, this invention provides a method for inhibiting the growth of tumors expressing an activated Ras oncogene by the administration of an effective amount of the above described compounds. Examples of tumors which may be inhibited include, but are not limited to, lung cancer (e.g., lung adenocarcinoma), pancreatic cancers (e.g., pancreatic carcinoma such as, for example, exocrine pancreatic carcinoma), colon cancers (e.g., colorectal carcinomas, such as, for example, colon adenocarcinoma and colon adenoma), myeloid leukemias (for example, acute myelogenous leukemia (AML)), thyroid follicular cancer, myelodysplastic syndrome (MDS), bladder carcinoma and epidermal carcinoma.

It is believed that this invention also provides a method for inhibiting proliferative diseases, both benign and malignant, wherein Ras proteins are aberrantly activated as a result of oncogenic mutation in other genes—i.e., the Ras gene itself is not activated by mutation to an oncogenic form—with said inhibition being accomplished by the administration of an effective amount of the carbonyl piperazinyl and piperidinyl compounds (1.0) described herein, to a mammal (e.g., a human) in need of such treatment. For example, the benign proliferative disorder neurofibromatosis, or tumors in which Ras is activated due to mutation or overexpression of tyrosine kinase oncogenes (e.g., neu, src, abl, lck, and fyn), may be inhibited by the carbonyl piperazinyl and piperidinyl compounds (1.0) described herein.

In another embodiment, the present invention is directed toward a method for inhibiting ras farnesyl protein transferase and the farnesylation of the oncogene protein Ras by administering an effective amount of compound (1.0) to mammals, especially humans. The administration of the compounds of this invention to patients, to inhibit farnesyl protein transferase, is useful in the treatment of the cancers described above.

DETAILED DESCRIPTION OF THE INVENTION

As used herein, the following terms are used as defined below unless otherwise indicated:

M+—represents the molecular ion of the molecule in the mass spectrum;

MH+—represents the molecular ion plus hydrogen of the molecule in the mass spectrum;

Bu—represents butyl;

Et—represents ethyl;

Me—represents methyl;

Ph—represents phenyl;

benzotriazol-1-yloxy represents

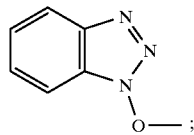

1-methyl-tetrazol-5-ylthio represents

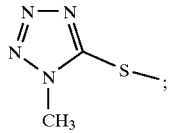

alkyl—(including the alkyl portions of alkoxy, alkylamino and dialkylamino)—represents straight and branched carbon chains and contains from one to twenty carbon atoms, preferably one to six carbon atoms; for example methyl, ethyl, propyl, iso-propyl, n-butyl, t-butyl, n-pentyl, isopentyl, hexyl and the like; wherein said alkyl group may be optionally and independently substituted with one, two, three or more of the following: halo, alkyl, aryl, alkoxy, amino, alkylamino, cyano, —$CF_3$, dialkylamino, hydroxy, oxy (=O), phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —CONR$^{10}$, —NCOR$^{10}$ or —COOR$^{10}$;

alkoxy—an alkyl moiety of one to 20 carbon atoms covalently bonded to an adjacent structural element through an oxygen atom, for example, methoxy, ethoxy, propoxy, butoxy, pentoxy, hexoxy and the like; wherein said alkoxy group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —CONR$^{10}$, —NCOR$^{10}$ or —COOR$^{10}$;

alkenyl—represents straight and branched carbon chains having at least one carbon to carbon double bond and containing from 2 to 12 carbon atoms, preferably from 2 to 6 carbon atoms and most preferably from 3 to 6 carbon atoms; wherein said alkenyl group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —CONR$^{10}$, —NCOR$^{10}$ or —COOR$^{10}$;

alkynyl—represents straight and branched carbon chains having at least one carbon to carbon triple bond and containing from 2 to 12 carbon atoms, preferably from 2 to 6 carbon atoms; wherein said alkynyl group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —SOR$_2$R$^{10}$, —SOR$^{10}$, —SR$^{10}$, —NHSO$_2$, —NO$_2$, —CONR$^{10}$, —NCOR$^{10}$ or —COOR$^{10}$;

aryl (including the aryl portion of aralkyl)—represents a carbocyclic group containing from 6 to 15 carbon atoms and having at least one aromatic ring (e.g., aryl is phenyl), wherein said aryl group optionally can be fused with aryl, cycloalkyl, heteroaryl or heterocycloalkyl rings; and wherein any of the available substitutable carbon and nitrogen atoms in said aryl group and/or said fused ring(s) may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —CONR$^{10}$, —NCOR$^{10}$ or —COOR$^{10}$;

aralkyl—represents an alkyl group, as defined above, wherein one or more hydrogen atoms of the alkyl moiety have been substituted with one or more aryl groups; wherein said aralkyl group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —CONR$^{10}$, —NCOR$^{10}$ or —COOR$^{10}$; Representative aralkyl groups include benzyl and diphenylmethyl;

cycloalkyl—represents saturated carbocyclic rings branched or unbranched of from 3 to 20 carbon atoms, preferably 3 to 7 carbon atoms; wherein said cycloalkyl group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, —NHSO$_2$, —NO$_2$, —CONR$^{10}$, —NCOR$^{10}$ or —COOR$^{10}$;

cycloalkylalkyl—represents an alkyl group, as defined above, wherein one or more hydrogen atoms of the alkyl moiety have been substituted with one or more cycloalkyl groups; wherein said cycloalkylalkyl group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$,—SO$_2$NHR$^{10}$,—SO$_2$R$^{10}$,—SOR$^{10}$,—SR$^{10}$, —NHSO$_2$, —NO$_2$, —CONR$^{10}$, —NCOR$^{10}$ or —COOR$^{10}$;

halo—represents fluoro, chloro, bromo and iodo;

heteroalkyl—represents straight and branched carbon chains containing from one to twenty carbon atoms, preferably one to six carbon atoms interrupted by 1 to 3 heteroatoms selected from —O—, —S—and —N—; wherein any of the available substitutable carbon and nitrogen atoms in said heteroalkyl chain may be optionally and independendently substituted with one, two, three or more of the following: halo, C$_1$–C$_6$ alkyl, aryl, cyano, hydroxy, alkoxy, oxy, phenoxy, —CF$_3$, —OCF$_3$, amino, alkylamino, dialkylamino, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, or —NHSO$_2$, —NO$_2$, —CONR$^{10}$, —NCOR$^{10}$ or —COOR$^{10}$;

heteroaryl—represents cyclic groups having at least one heteroatom selected from O, S and N, said heteroatom(s) interrupting a carbocyclic ring structure and having a sufficient number of delocalized pi electrons to provide aromatic character, with the aromatic heterocyclic groups containing from 2 to 14 carbon atoms,wherein said heteroaryl group optionally can be fused with one or more aryl, cycloalkyl, heteroaryl or heterocycloalkyl rings; and wherein any of the available substitutable carbon or nitrogen atoms in said heteroaryl group and/or said fused ring(s) may be optionally and independendently substituted with one, two, three or more of the following: halo, C$_1$–C$_6$ alkyl, aryl, cyano, hydroxy, alkoxy, oxy, phenoxy, —CF$_3$, —OCF$_3$, amino, alkylamino, dialkylamino, heterocycloalkyl, —SO$_2$NH$_2$, —NHSO$_2$R$^{10}$, —SO$_2$NHR$^{10}$, —SO$_2$R$^{10}$, —SOR$^{10}$, —SR$^{10}$, or —NHSO$_2$, —NO$_2$, —CONR$^{10}$, —NCOR$^{10}$ or —COOR$^{10}$. Representative heteroaryl groups can include, for example, furanyl, imidazoyl, pyrimidinyl, triazolyl, 2-, 3- or 4-pyridyl or 2-, 3- or 4-pyridyl N-oxide wherein pyridyl N—oxide can be represented as:

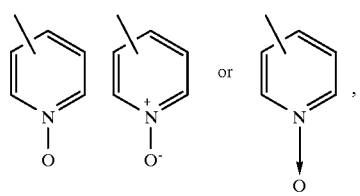

heteroarylalkyl—represents an alkyl group, as defined above, wherein one or more hydrogen atoms have been replaced by one or more heteroaryl groups; wherein said heteroarylalkyl group may be optionally and independently substituted with one, two, three or more of the following: halo, alkyl, aryl, alkoxy, amino, alkylamino, cyano, —CF$_3$, dialkylamino, hydroxy, oxy, phenoxy, —OCF$_3$, heterocycloalkyl, —SO$_2$NH$_2$, —NHSO$_2$R$^{10}$, —SO$_2$NHR$^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$; as exemplified by 2-, 3- or 4-pyridylmethyl or 2-, 3- or 4-pyridylmethyl N-oxide;

heterocycloalkyl—represents a saturated, branched or unbranched carbocylic ring containing from 3 to 15 carbon atoms, preferably from 4 to 6 carbon atoms, which carbocyclic ring is interrupted by 1 to 3 heteroatoms selected from —O—, —S—and —N—, wherein optionally, said ring may contain one or two unsaturated bonds which do not impart aromatic character to the ring; and wherein any of the available substitutable carbon and nitrogen atoms in the ring may be optionally and independently substituted with one, two, three or more of the following: halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$. Representative heterocycloalkyl groups can include 2- or 3-tetrahydrofuranyl, 2- or 3-tetrahydrothienyl, 1-, 2-, 3- or 4-piperidinyl, 2- or 3-pyrrolidinyl, 1-, 2- or 3-piperizinyl, 2- or 4-dioxanyl, morpholinyl,

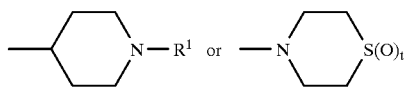

wherein $R^1$ is defined hereinbefore and t is 0, 1 or 2.

heterocycloalkylalkyl—represents an alkyl group, as defined above, herein one or more hydrogen atoms have been replaced by one or more eterocycloalkyl groups; wherein optionally, said ring may contain one or wo unsaturated bonds which do not impart aromatic character to the ring; and wherein said heterocycloalkylalkyl group may be optionally and independently substituted with one, two, three or more of the following:. halo, alkyl, aryl, alkoxy, amino, alkylamino, cyano, —$CF_3$, dialkylamino, hydroxy, oxy, phenoxy, —$OCF_3$, heterocycloalkyl, —$SO_2NH_2$, —$NHSO_2R^{10}$, —$SO_2NHR^{10}$, —$SO_2R^{10}$, —$SOR^{10}$, —$SR^{10}$, —$NHSO_2$, —$NO_2$, —$CONR^{10}$, —$NCOR^{10}$ or —$COOR^{10}$.

The following solvents and reagents are referred to herein by the abbreviations indicated: tetrahydrofuran (THF); ethanol (EtOH); methanol (MeOH); acetic acid (HOAc or AcOH); ethyl acetate (EtOAc); N,N-dimethylformamide (DMF); trifluoroacetic acid (TFA); trifluoroacetic anhydride (TFAA); 1-hydroxybenzotriazole (HOBT); m-chloroperbenzoic acid (MCPBA); triethylamine ($Et_3N$); diethyl ether ($Et_2O$); ethyl chloroformate ($ClCO_2Et$); and 1-(3-dimethylaminopropyl)-3-ethyl carbodiimide hydrochloride (DEC).

Reference to the position of the substituents $R^1$, $R^2$, $R^3$, and $R^4$ is based on the numbered ring structure:

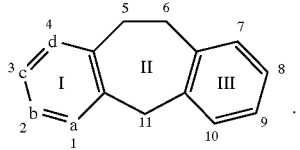

Certain compounds of the invention may exist in different stereoisomeric forms (e.g., enantiomers and diastereoisomers). The invention contemplates all such stereoisomers both in pure form and in mixture, including racemic mixtures. For example, the carbon atom at the C-11 position can be in the S or R stereoconfiguration.

Certain tricyclic compounds will be acidic in nature, e.g. those compounds which possess a carboxyl or phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic tricyclic compounds also form pharmaceutically acceptable salts, e.g., acid addition salts. For example, the pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purpopses of the invention.

Compounds of the invention may be made by the methods described in the examples below, and by the methods described in WO 95/10516 published Apr. 20, 1995—see, for example, the methods for preparing compounds of Formula 400.00.

On page 57 at lines 7 to 16 of WO 95/10516 a process is disclosed for introducing substituents at the C-3 position of pyridine Ring I of Formula 1.0 by nitrating a compound of Formula 415.00. The nitro group may then be reduced to the corresponding amine using the disclosed reagents or powdered Zn and either $CuCl_2$ or $CuBr_2$ in aqueous EtOH . Compounds of the present invention can be prepared according to the following Scheme I:

Scheme I

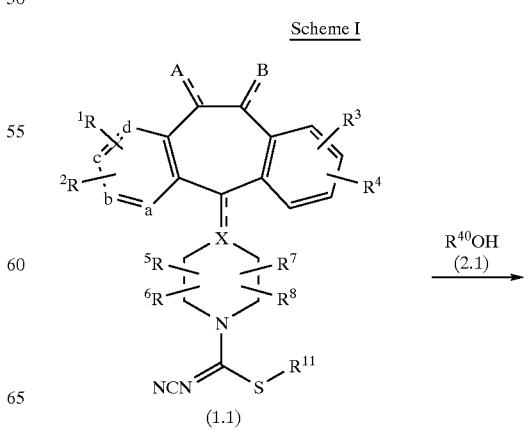

-continued

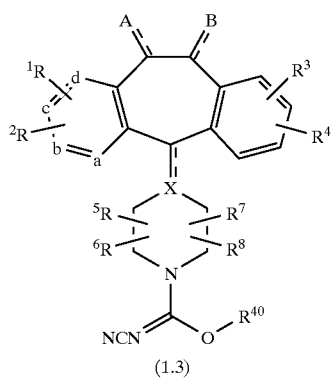

(1.3)

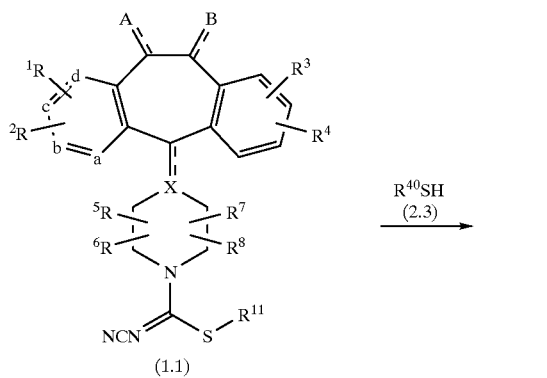

(1.1)

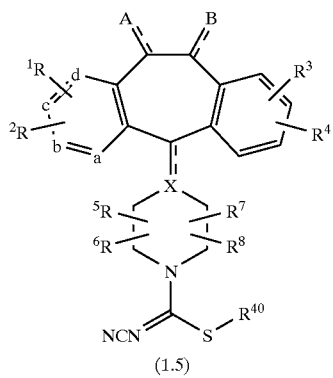

(2.0)

-continued

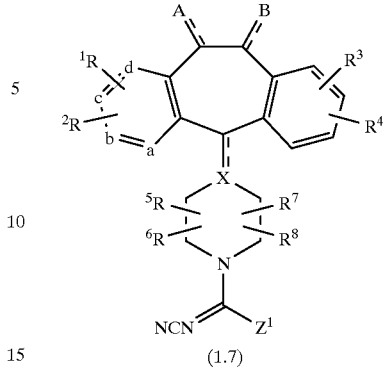

(1.7)

wherein $Z^1$ represents alkyl, aryl, aralkyl, heteroalkyl, heteroaryl, heteroarylalkyl, heterocycloalkyl, heterocycloalkylalkyl and —$CR^{40}R^{42}$; the dotted line represents a single or double bond; and a, b, c, d, A, B, $R^1$, $R^2$, $R^3$, $R^4$, $R^5$, $R^6$, $R^7$, $R^8$, $R^8$, $R^{11}$, $R^{40}$ and $R^{42}$ are as. defined hereinbefore.

Referring to the Scheme I, compounds of formula (1.3) can be prepared by reacting the compounds of formula (1.1), preferably where $R^{11}$ is alkyl such as methyl, with alcohol ($R^{40}$OH) of formula (2.1) in the presence of a suitable base, and optional non-protic solvent, in amounts and under conditions effective to give compounds (1.3). Suitable bases include organic bases such as pyridine and triethylamine; or inorganic bases of alkali and alkaline earth metals including carbonates such as sodium, lithium, potassium and cesium carbonates, hydroxides such as sodium and potassium hydroxides; hydrides such as sodium or potassium hydride; and sodium t-butoxide, preferably sodium hydride. Suitable non-protic solvents include ethers, dimethyformamide (DMF), dimethylsulfoxide (DMSO), tetrahydrofuran (THF), dimethoxyethane (DME) and mixtures thereof, preferably DMF. Alternatively, the reaction can be carried out neat, using an excess of the alcohol. The amounts of alcohol (2.1) can range from about 1 to about 10 moles per mole of compound (1.1). Temperatures can range from 0° to 100° C., or reflux of the reaction mixture.

Compounds of formula (1.5) can be prepared by reacting the compounds of formula (1.1) with thiol ($R^{40}$SH) of formula (1.1) in the presence of a suitable base, and optional non—protic solvent to give compounds (1.5), using reaction conditions as described for preparing compounds (1.3), above.

Compounds of formula (1.7) can be prepared by reacting the compounds of formula (2.0) with N-cyanoimidate of formula (2.7) in the presence of an optional non-protic solvent to give compounds (1.7), using reaction conditions as described for preparing compounds (1.3), above. Compounds of the present invention can be prepared according to the following Scheme II:

Scheme II
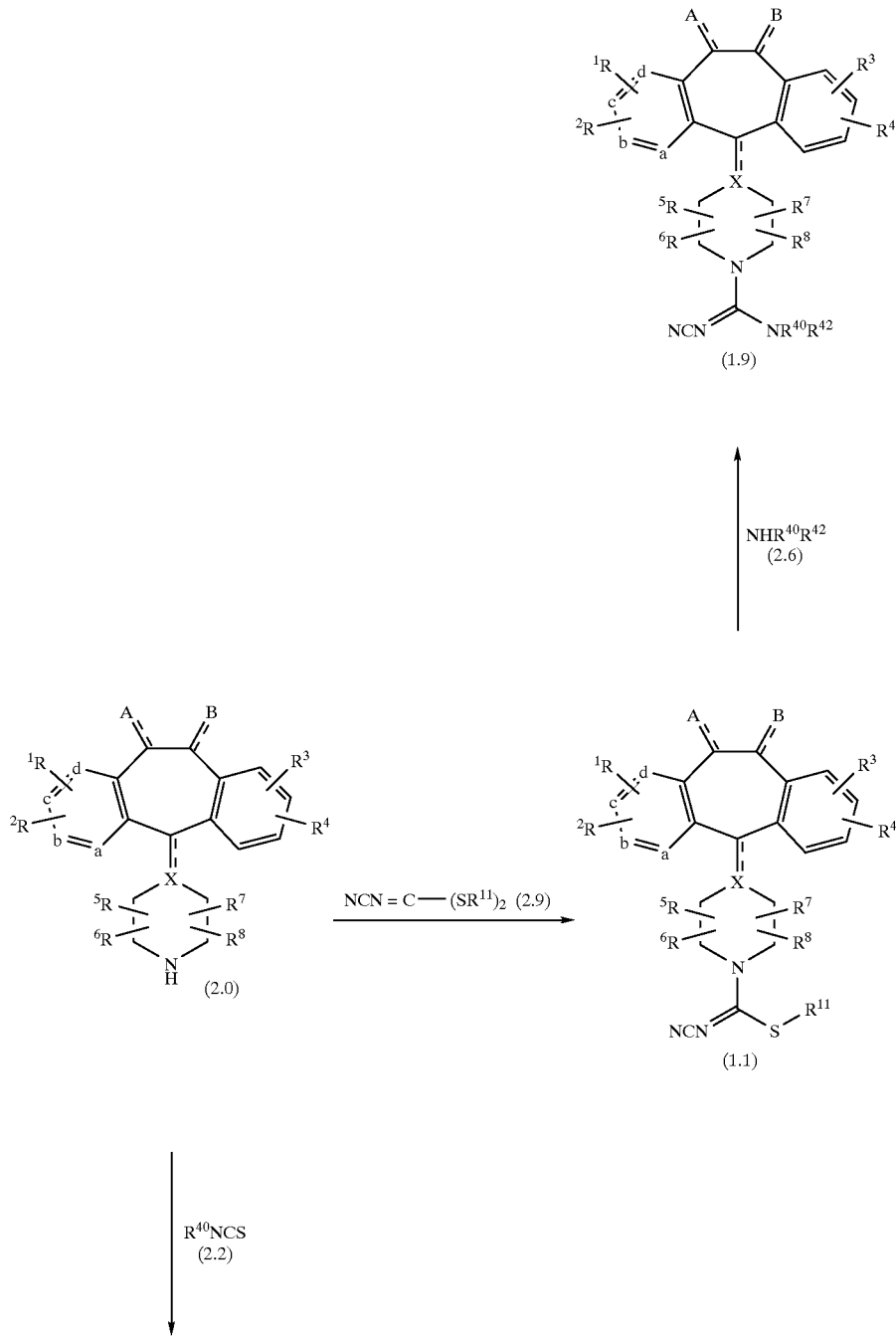

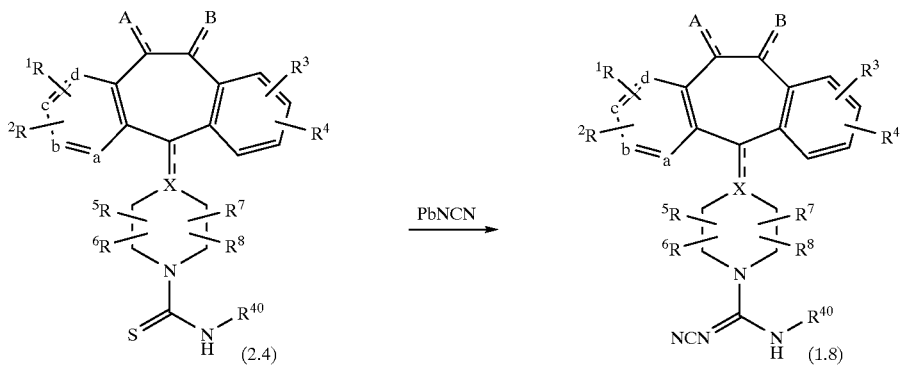

wherein a, b, c, d, A, B, $R^1$, $R^2$, $R^3$, $R^4$, $R^5$, $R^6$, $R^7$, $R^8$, $R^8$, $R^{11}$, $R^{40}$ and $R^{42}$ are as defined hereinbefore; and the dotted line represents a single or double bond.

Referring to the Scheme II, compounds of formula (1.1) can be prepared by reacting the compounds of formula (2.0) with N-cyanodithioiminocarbonate (NCN=C—(SR$^{11}$)$_2$ of formula (2.9) in the presence of a suitable protic or non—protic solvent, in amounts and under conditions effective to give compounds (1.1). Suitable protic solvents include $C_{1-10}$ alkanols, such as methanol, ethanol, propanol, hexanol, octanol, decanol and the like. Suitable non-protic solvents are described hereinbefore. The amounts of N-cyanodithioiminocarbonate (2.9) can range from about 1 to about 10 moles per mole of compound (2.0). Temperatures can range from 0° to 100° C., or reflux of the reaction mixture.

Compounds of formula (1.9) can be prepared by reacting the compounds of formula (1.1) with amine (NHR$^{40}$R$^{42}$) of formula (2.6) with an optional base and/or optional protic or aprotic solvent such as those described hereinbefore. In a first procedure, compound (1.1) is reacted with amine (2.6) neat, at temperatures ranging from about 50° to 80° C. In a second procedure, compound (1.1) is reacted with about equimolar amounts of amine (2.6) in the presence of a base such as sodium hydride and an aprotic solvent such as DMSO or DMF. In a third procedure, compound (1.1) is reacted with excess amine (2.6) in an protic solvent such as ethanol. In a fourth procedure, compound (1.1) is reacted with amine (2.6) neat, using catalytic amounts of base, such as sodium hydride. In a fifth procedure, compound (1.1) is reacted with greater than two equivalents of amine (2.6) in an aprotic solvent such as DMF at a temperature of about 75° C. Except as noted otherwise, temperatures can range from 0° to 100° C., or reflux of the reaction mixture and amounts of amine (2.6) can range from 1 to about 10 moles per mole of compound (1.1).

Compounds of formula (2.4) can be prepared by reacting the compounds of formula (2.0) with isothiocyanate (R$^{40}$NCS) of formula (2.2) in the presence of a suitable non—protic solvent in amounts and under conditions effective to give compounds (2.4). Suitable non-protic solvents are described hereinbefore. The amounts of isothiocyanate (2.2) can range from about 1 to about 10 moles per mole of compound (2.0). Temperatures can range from 0° to 100° C., or reflux of the reaction mixture.

Compounds of formula (1.8) can be prepared by reacting the compounds of formula (2.4) with lead cyanamine (PbNCN) in the presence of a suitable non-protic solvent in amounts and under conditions effective to give compounds (2.4). Suitable non-protic solvents are described hereinbefore, preferably DMF. The amounts of lead cyanamine can range from about 1 to about 10 moles per mole of compound (2.4). Temperatures can range from 0° to 100° C., or reflux of the reaction mixture.

Compound of fomula 1.0 can be isolated from the reaction mixture using conventional procedures, such as, for example, extraction of the reaction mixture from water with organic solvents, evaporation of the organic solvents, followed by chromatography on silica gel or other suitable chromatographic media.

Compounds of the present invention and preparative starting E materials therof, are exemplified by the following examples, which should not be construed as limiting the scope of the disclosure.

EXAMPLE 1

Methyl 4-(3-bromo-8-chloro-5,6-dihydro-11 H-benzo [5.6]cyclohepta[1 ,2-b]pyridin-11-ylidene)—B-cyano-1-piperidinecarboximidothioate

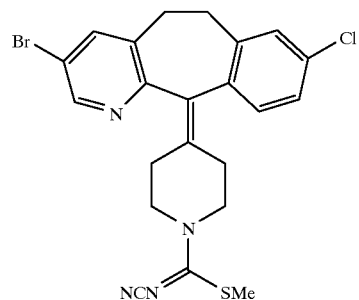

Dissolve 4-(3-bromo-8-chloro-5,6-dihydro-11H-benzo[5.6] cyclohepta[1,2-b]pyridin-11-ylidene)-1-piperidine (40 gm, 0.1 mol) in 600 mL of absolute ethanol. Add dimethyl N-cyanodithioiminocarbonate (16.5 gm, 0.11 mol) and reflux under a dry nitrogen atmosphere for two hours. Evaporate to dryness to obtain a brown foamy solid. Chromatograph on silica gel using 25% to 50% ethylacetatelhexanes as the eluent to obtain 50.8 gm of title compound. FABMS M+1=489

EXAMPLE 2

Ethyl 4-[[[4-(3-bromo-8-chloro-5,6-dihydro-11H-benzo[5.6]cyclohepta[1,2-b]pyridin-11-ylidene)-1-piperidinyl](cyanoimino)methyl]amino]-1-piperidinecarboxylate

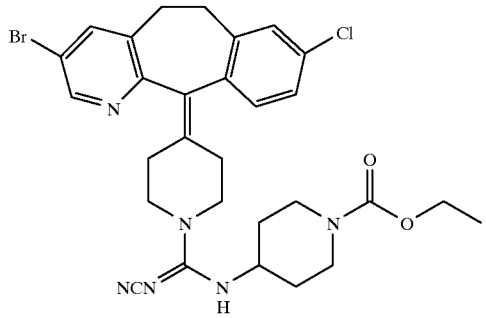

Dissolve methyl 4-(3-bromo-8-chloro-5,6-dihydro-11H-benzo[5.6]cyclohepta[1,2-b]pyridin-11-ylidene)-B-cyano-1-piperidinecarboximidothioate (0.1 gm, 0.20 mmol) in 1 ml of ethyl 4-amino-1-piperidinecarboxylate. Stir at 100° C. for 18 hours. Let cool to room temperature. Add the mixture to water and filter the resulting solids. Dissolve the solid in methylene chloride and chromatograph on silica gel using 5% methanol/methylene chloride as eluent to obtain 0.15 gm (34%) of title product. FABMS M+1=613

EXAMPLE 3

[[4-(3-bromo-8-chloro-5,6-dihydro-11H-benzo[5.6]cyclohepta[1,2-b]pyridin-11-ylidene)-1-piperidinyl](4-pyridinylamino)methylene]cyanamide N1-oxide

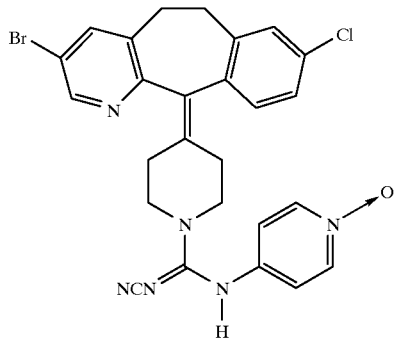

Dissolve methyl 4-(3-bromo-8-chloro-5,6-dihydro-11H-benzo[5.6]cyclohepta[1,2-b]pyridin-11-ylidene)-B-cyano-1-piperidinecarboximidothioate (0.3 g, 0.60 mmole) and 4-aminopyridyl-N-oxide (0.07 gm, 0.60 mmol) in 5 mL of dimethylsulfoxide under a dry nitrogen atmosphere at ambient temperature. Add sodium hydride as a 60% oil dispersion (24 mg, 0.6 mmol) portionwise while stirring. After stirring 2 hours, add the reaction mixture to brine and extract with 20 mL of methylene chloride three times. Combine the extracts, dry over magnesium sulfate, filter and evaporate to an oil. Chromatograph the oil on a silica gel coloumn using 2% to 10% methanol in methylene chloride to obtain 0.15 g (47%) of title compound as a solid. FABMS M+1=549.1

EXAMPLE 4

[[4-(3-bromo-8-chloro-5,6-dihydro-11H-benzo[5,6]cyclohepta[1,2-b]pyridin-11-ylidene)-1-piperidinyl][cyclopropylamino]methylene] cyanamide

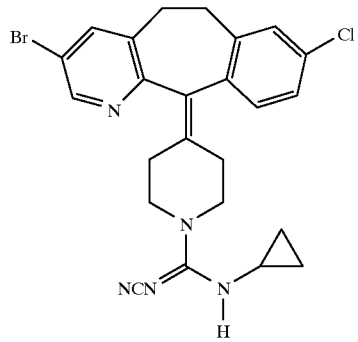

Dissolve methyl 4-(3-bromo-8-chloro-5,6-dihydro-11H-benzo[5.6]cyclohepta[1,2-b]pyridin-11-ylidene)-B-cyano-1-piperidinecarboximidothioate (0.15 gm, 0.31 mmol) in 3 mL of absolute ethanol. Add cyclopropylamine (0.3 mL, 4.30 mmol) and stir at ambient temperature. After 24 hours, add the reaction mixture to brine and extract with 20 mL of methylene chloride three times. Combine the extracts, dry over magnesium sulfate, filter and evaporate to an oil. Chromatograph the oil on a silica gel coloumn using 2% to 10% methanol in methylene chloride to obtain 0.133 gm (86%) of the title compound as a solid. FABMS M+1=498.

EXAMPLE 5

[[4-(3-bromo-8-chloro-5,6-dihydro-11H-benzo[5.6]cyclohepta[1,2-b]pyridin-11-ylidenyl[[(4-methoxyphenyl)methyl] amino] methylene] cyanamide

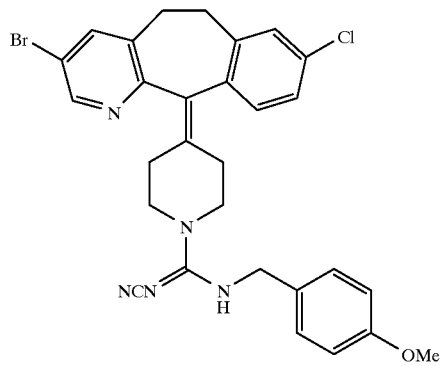

Dissolve methyl 4-(3-bromo-8-chloro-5,6-dihydro-11H-benzo[5.6]cyclohepta[1,2-b]pyridin-11-ylidene)-B-cyano-1-piperidinecarboximidothioate (0.5 gm, 1.02 mmol) in 5 mL of DMF. Add 4-methoxybenzylamine (0.4 mL, 2.9 mmol) and stir at 75° C. for 24 hours. Add to brine and extract with ethyl acetate three times. Dry the extract over magnesium sulfate, filter, and evaporate to dryness. Chromatograph on silica gel using 5% methanol/methylene chloride as eluent to obtain 0.4 gm, (68%) of title compound. FABMS M+1=578

EXAMPLE 6

[[4-(3-bromo-8-chloro-5,6-dihydro-11H-benzo[5.6] cyclohepta[1,2-b]pyridin-11-ylidene)-1-piperidinyl] [(4-fluorophenyl)amino]methylene]cyanamide

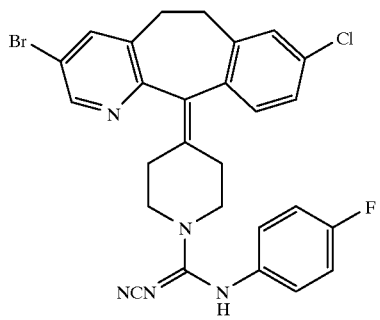

Dissolve methyl 4-(3-bromo-8-chloro-5,6-dihydro-11H-benzo[5.6]cyclohepta[1,2-b]pyridin-11-ylidene)-B-cyano-1-piperidinecarboximidothioate (0.25 gm, 0.51 mmol) in 2.5 mL of 4-fluoroanaline. While stirring under a dry nitrogen atmosphere add approximately 10 mg of sodium hydride and stir at 100° C. for 1 hr. Let cool to room temperature. Add to brine and extract with ethyl acetate three times. Dry the extract over magnesium sulfate, filter, and evaporate to dryness and chromatograph on silica gel using 5% methanol/ methylene chloride as eluent to obtain 0.155 gm (55%) of title compound. FABMS M+1=552.

EXAMPLE 7

[[(4H-1,3-benzodioxin-6-yl) amino] [4-(3-bromo-8-chloro-5,6-dihydro-11H-benzo[5,6]cyclohepta[1,2-b] pyridin-11 -ylidene)-1-piperidinyl] methylene] cyanamide

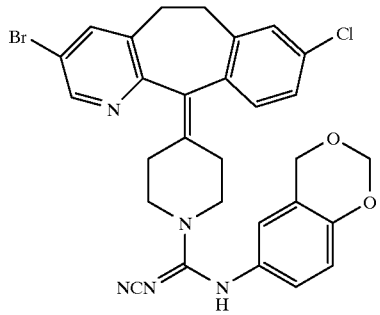

Dissolve 4-(3-bromo-8-chloro-5,6-dihydro-11H-benzo[5.6] cyclohepta[1,2-b]pyridin-11-ylidene)-N-(4H-1,3-benzodioxin-6-yl)-1-piperidinecarbothioamide (0.1 gm, 0.198 mmol) in dry N,N-dimethylformamide (DMF). Add lead cyanamide (98 mg, 0.39 mmol) and benzyltriethylammonium chloride (5 mg) and stir at 90° C. for 2 days.). Add lead cyanamide (98 mg, 0.39 mmol) and benzyltriethylammonium chloride (5 mg) again and sitr for 24 hrs. Add to brine and extract with ethyl acetate three times. Dry the extract over magnesium sulfate, filter, and evaporate to dryness. Chromatograph on silica gel using 5% methanol/ methylene chloride as eluent to obtain 39 mg (38%) of title compound. FABMS M+1=701

EXAMPLE 8

[[4-(3, 10-dibromo-8-chloro-5,6-dihydro-11H-benzo[5.6] cyclohepta[1,2-b]pyridin-11-ylidene)-1-piperidinyl](3-pyridyinyl)methylene]cyanamide

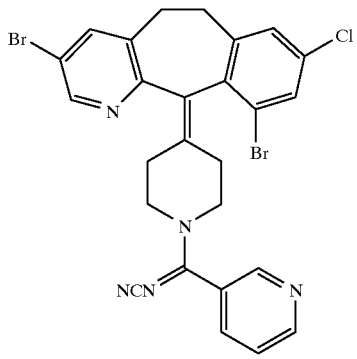

Dissolve 4-(3,10-dibromo-8-chloro-5,6-dihydro-11H-benzo [5.6]cyclohepta[1,2-b]pyridin-11-ylidene)-1-piperidine (0.2 gm, 0.43 mmol) in 2 mL of DMF. Add isopropyl-N-cyano-3-pyridylimidate [ref: Chem. Pharm. Bull. 42(12) 2475 (1994)] (0.16gm, 0.86 mmol) and stir at 75° C. for 24 hours. Add to brine and extract with ethyl acetate three times. Dry the extract over magnesium sulfate, filter, and evaporate to dryness. Chromatograph on silica gel using 5% methanol/ methylene chloride as eluent to obtain 0.16 gm of title compound. FABMS M+1=599.

EXAMPLE 9

N-cyano-4-(3,10-dibromo-8-chloro-6,11-dihydro-5h-benzo[5,6]cyclohepta[1,2-b]pyridin-11-yl)-n'-(3-pyridinylmethyl)-1-piperidinecarboximidamide n1-oxide

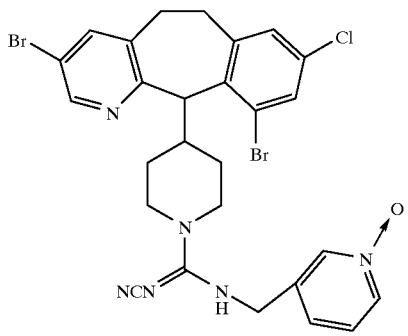

Dissolve methyl 4-(3-bromo-8-chloro-5,6-dihydro-11H-benzo[5.6]cyclohepta[1,2-b]pyridin-11-ylidene)-B-cyano-1-piperidinecarboximidothioate (1.0 g, 1.76 mmole) and 3-aminomethylpyridyl-N-oxide (0..65 gm, 5.8 mmol) in 10 mL of N,N-dimethylformamide under a dry nitrogen atmosphere at 135° C. while stirring. After stirring 2 hours, add the reaction mixture to brine and extract with 20 mL of methylene chloride three times. Combine the extracts, dry over magnesium sulfate, filter and evaporate to an oil. Chromatograph the oil on a silica gel coloumn using 2% to 10% methanol in methylene chloride to obtain 0.23 g of title compound as a solid. FABMS M+1=563

Using the processes described above and substituting appropriate reagents, the compounds described in the following table are prepared.

| Example No. | Product Compound | FPT IC$_{50}$ (uM) | COS IC$_{50}$ (uM) |
|---|---|---|---|
| 10 | | 0.018 | 0.25 |
| 11 | | 0.015 | 0.25 |
| 12 | | <0.41 | |
| 13 | | 0.72 | |

-continued

| Example No. | Product Compound | FPT IC$_{50}$ (uM) | COS IC$_{50}$ (uM) |
|---|---|---|---|
| 14 | | 0.086 | 2.5 |
| 15 | | 0.042 | 0.56 |
| 16 | | 0.054 | 2.3 |
| 17 | | 0.26 | 5.0 |

-continued

| Example No. | Product Compound | FPT IC$_{50}$ (uM) | COS IC$_{50}$ (uM) |
|---|---|---|---|
| 18 | | 0.038 | 0.8 |
| 19 | | 0.020 | 0.48 |
| 20 | | 0.105 | 1.6 |
| 21 | | 0.124 | |

-continued

| Example No. | Product Compound | FPT IC$_{50}$ (uM) | COS IC$_{50}$ (uM) |
|---|---|---|---|
| 22 | | 0.17 | |
| 23 | | 0.14 | 2.4 |
| 24 | | 0.010 | <0.25 |
| 25 | | 0.043 | 0.27 |

-continued

| Example No. | Product Compound | FPT IC$_{50}$ (uM) | COS IC$_{50}$ (uM) |
| --- | --- | --- | --- |
| 26 | | 0.029 | 0.75 |
| 27 | | 0.017 | 2.6 |
| 28 | | 0.013 | |
| 29 | | 0.038 | 0.57 |

-continued

| Example No. | Product Compound | FPT IC$_{50}$ (uM) | COS IC$_{50}$ (uM) |
|---|---|---|---|
| 30 | | 0.155 | |
| 31 | | 0.26 | |
| 32 | | 0.27 | |
| 33 | | 2.8 | |

-continued
| Example No. | Product Compound | FPT IC$_{50}$ (uM) | COS IC$_{50}$ (uM) |
|---|---|---|---|
| 34 | 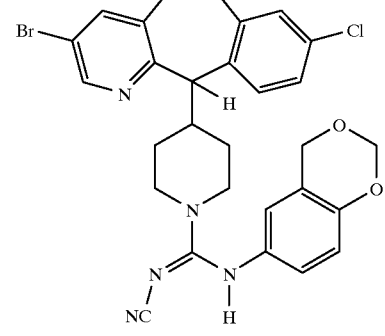 | 9.6 | |
| 35 | 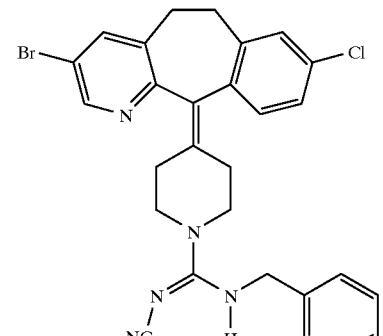 | 0.23 | |
| 36 | 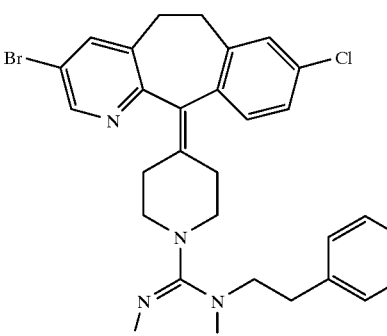 | 0.03 | 0.28 |
| 37 | 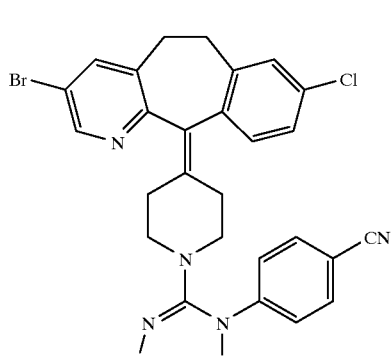 | 0.032 | 0.28 |

-continued

| Example No. | Product Compound | FPT IC$_{50}$ (uM) | COS IC$_{50}$ (uM) |
|---|---|---|---|
| 38 | | 0.32 | |
| 39 | | 0.15 | |
| 40 | | 0.199 | |
| 41 | | 0.015 | 0.7 |

-continued
| Example No. | Product Compound | FPT IC$_{50}$ (uM) | COS IC$_{50}$ (uM) |
|---|---|---|---|
| 42 | 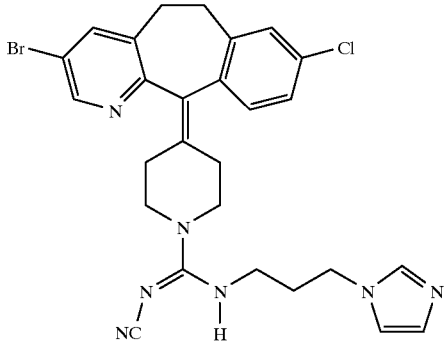 | 0.035 | 4.0 |
| 43 | 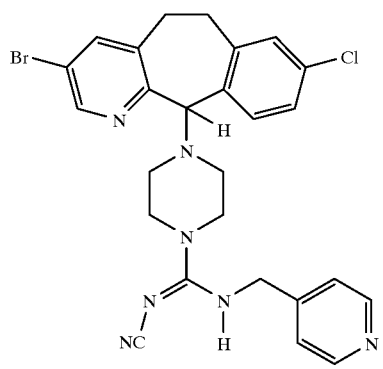 | 0.011 | |
| 44 | 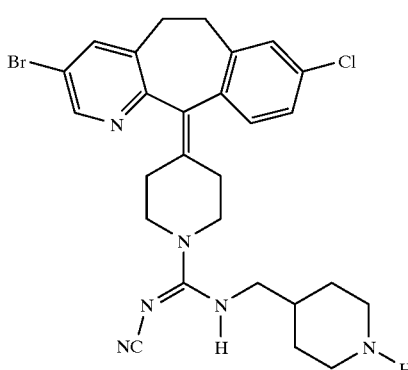 | 0.018 | |
| 45 | 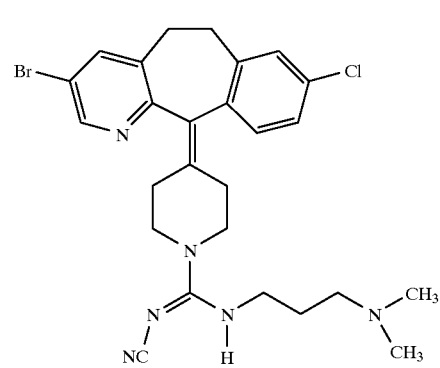 | 0.074 | |

-continued

| Example No. | Product Compound | FPT IC$_{50}$ (uM) | COS IC$_{50}$ (uM) |
|---|---|---|---|
| 46 | | 0.15 | |
| 47 | | 0.014 | |
| 48 | | 0.064 | |
| 49 | | 0.013 | |

-continued

| Example No. | Product Compound | FPT IC$_{50}$ (uM) | COS IC$_{50}$ (uM) |
|---|---|---|---|
| 50 | | 0.3 | |
| 51 | | 0.073 | |
| 52 | | 0.024 | |
| 53 | | 0.087 | |

-continued

| Example No. | Product Compound | FPT IC$_{50}$ (uM) | COS IC$_{50}$ (uM) |
|---|---|---|---|
| 54 | | | >0.11 |
| 55 | | | 0.11 |
| 56 | | | 0.042 |
| 57 | | | 0.31 |

-continued
| Example No. | Product Compound | FPT IC$_{50}$ (uM) | COS IC$_{50}$ (uM) |
|---|---|---|---|
| 58 | 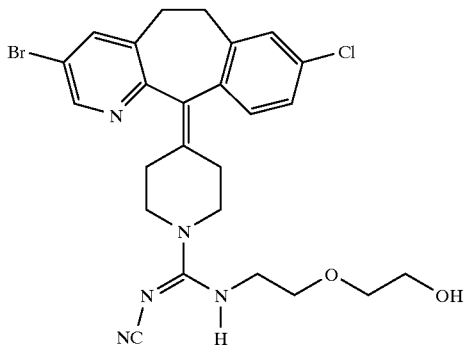 | 0.084 | |
| 59 | 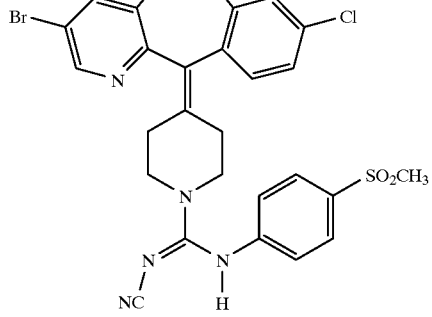 | 0.087 | |
| 60 | 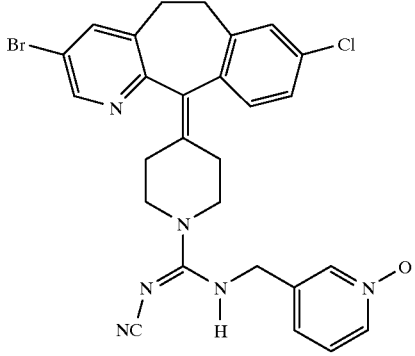 | 0.012 | >1.0 |
| 61 | 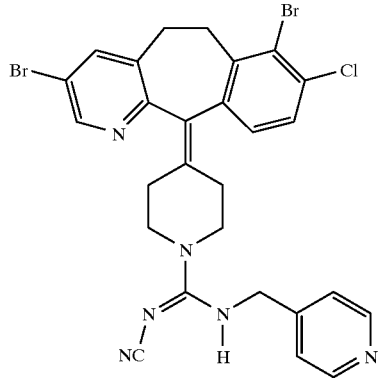 | 0.005 | |

-continued

| Example No. | Product Compound | FPT IC$_{50}$ (uM) | COS IC$_{50}$ (uM) |
|---|---|---|---|
| 62 | | | 0.058 |
| 63 | | | 0.006 |
| 64 | | | >0.95 |
| 65 | | | 0.116 |

-continued

| Example No. | Product Compound | FPT IC$_{50}$ (uM) | COS IC$_{50}$ (uM) |
|---|---|---|---|
| 66 | | | 0.014 |
| 67 | | | 0.0017 |
| 68 | | | 0.007 |

-continued

| Example No. | Product Compound | FPT IC$_{50}$ (uM) | COS IC$_{50}$ (uM) |
|---|---|---|---|
| 69 | | 0.0037 | |
| 70 | | 0.006 | 16 |
| 71 | | 0.043 | |
| 72 | | >0.10 | |

-continued
| Example No. | Product Compound | FPT IC$_{50}$ (uM) | COS IC$_{50}$ (uM) |
|---|---|---|---|
| 73 | 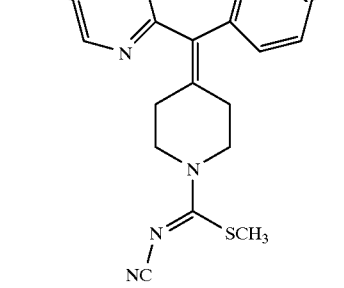 | 0.026 | |
| 74 | 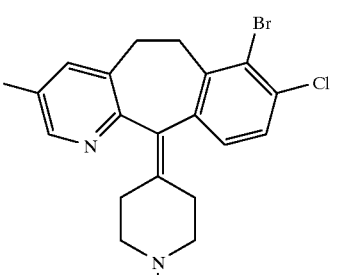 | 0.015 | |
| 75 | 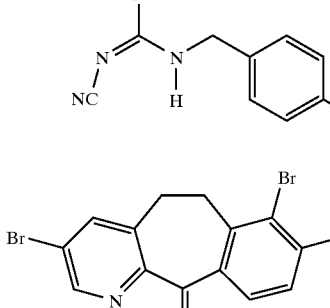 | 0.0048 | |
| 76 | 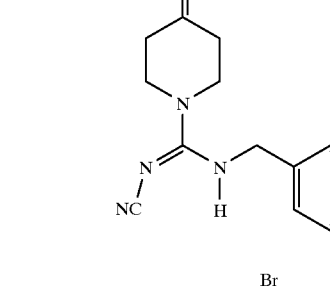 | 0.0047 | |

-continued

| Example No. | Product Compound | FPT IC$_{50}$ (uM) | COS IC$_{50}$ (uM) |
|---|---|---|---|
| 77 | | 0.0044 | |
| 78 | | 0.064 | |
| 79 | | 0.10 | |

| Example No. | Product Compound | FPT IC$_{50}$ (uM) | COS IC$_{50}$ (uM) |
|---|---|---|---|
| 80 | | 0.038 | |
| 81 | | 0.0046 | |
| 82 | | 0.0017 | |
| 83 | | >0.033 | |

PREPARATION OF STARTING MATERIALS

Starting materials useful in preparing the compounds of the present invention are exemplified by the following preparative examples, which should not be construed to limit the scope of the disclosure. The tricylic compounds used starting materials, such as compound (2.0), inorganic and organic bases, N-cyanoimidates and alcohols can be prepared using known methods in the art, such as taught in U.S. Pat. Nos. 5,089,496; 5,151,423; 4,454,143; 4,355,036; PCT /US94/11390 (WO95/10514); PCT/US94/11391 (WO 95/10515); PCT/US94/11392 (WO95/10516); Stanley R. Sandler and Wolf Karo, Organic Functional Group Preparations, 2nd Edition, Academic Press, Inc., San Diego, Calif., Vol. 1–3, (1983), and in J. March, Advanced Organic Chemistry, Reactions & Mechanisms, and Structure, 3rd Edition, John Wiley & Sons, New York, 1346 pp. (1985). Alternative mechanistic pathways and analogous structures within the scope of the invention may be apparent to those skilled in the art.

PREPARATIVE EXAMPLE 7

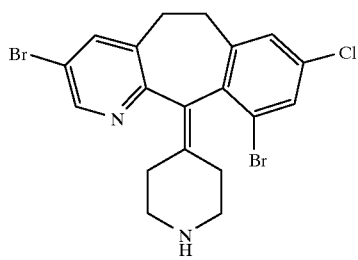

Step A:

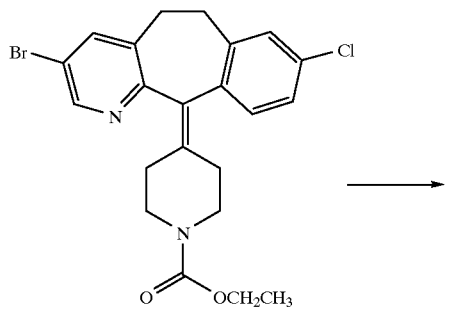

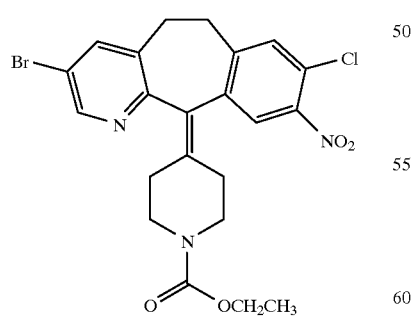

Combine 15 g (38.5 mmol) of 4-(8-chloro-3-bromo-5,6-dihydro-11 H-benzo[5,6]cyclohepta[1,2-b]pyridin-11-ylidene)-1-piperidine-1-carboxylic acid ethyl ester and 150 mL of concentrated $H_2SO_4$ at −5° C., then add 3.89 g (38.5 mmol) of $KNO_3$ and stir for 4 hours. Pour the mixture into 3 L of ice and basify with 50% NaOH (aqueous). Extract with $CH_2Cl_2$, dry over MgSO4, then filter and concentrate in vacuo to a residue. Recrystallize the residue from acetone to give 6.69 g of the product.

Step B:

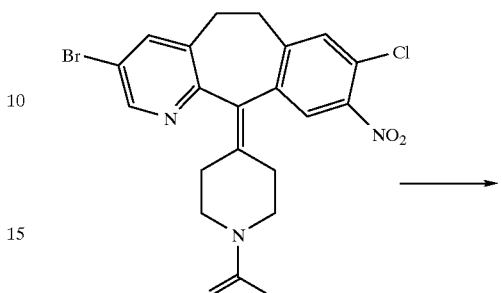

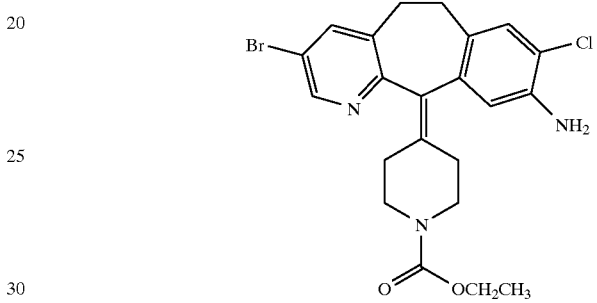

Combine 6.69 g (13.1 mmol) of the product of Step A and 100 mL of 85% EtOH/water, then add 0.66 g (5.9 mmol) of $CaCl_2$ and 6.56 g (117.9 mmol) of Fe and heat the mixture at reflux overnight. Filter the hot reaction mixture through celite® and rinse the filter cake with hot EtOH. Concentrate the filtrate in vacuo to give 7.72 g of the product.

Step C:

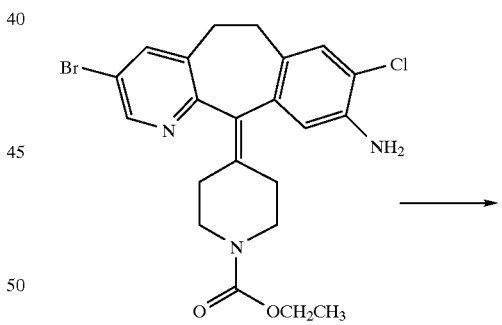

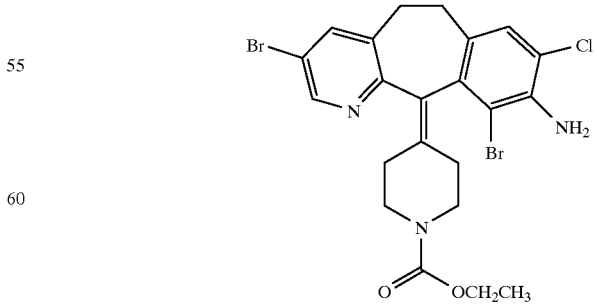

Combine 7.70 g of the product of Step B and 35 mL of HOAc, then add 45 mL of a solution of $Br_2$ in HOAc and stir the mixture at room temperature overnight. Add 300 mL of 1 N NaOH (aqueous), then 75 mL of 50% NaOH (aqueous) and extract with EtOAc. Dry the extract over MgSO and concentrate in vacuo to a residue. Chromatograph the residue (silica gel, 20%–30% EtOAc/hexane) to give 3.47 g of the product (along with another 1.28 g of partially purified product).

Step D:

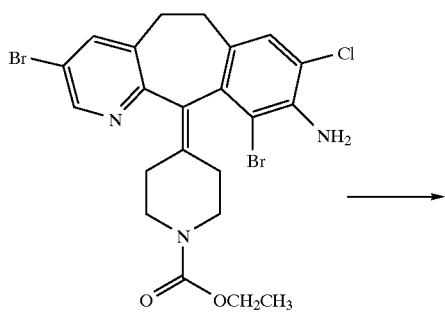

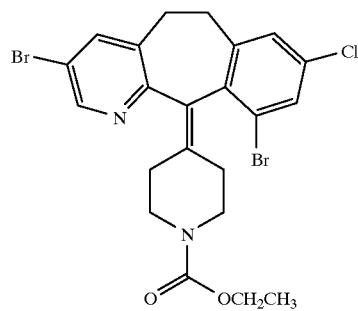

Combine 0.557 g (5.4 mmol) of t-butyinitrite and 3 mL of DMF, and heat the mixtre at to 60°–70° C. Slowly add (dropwise) a mixture of 2.00 g (3.6 mmol) of the product of Step C and 4 mL of DMF, then cool the mixture to room temperature. Add another 0.64 mL of t-butyinitrite at 40° C. and reheat the mixture to 60°–70° C. for 0.5 hrs. Cool to room temperature and pour the mixture into 150 mL of water. Extract with CH₂Cl₂, dry the extract over MgSO₄ and concentrate in vacuo to a residue. Chromatograph the residue (silica gel, 10%–20% EtOAc/hexane) to give 0.74 g of the product.

Step E:

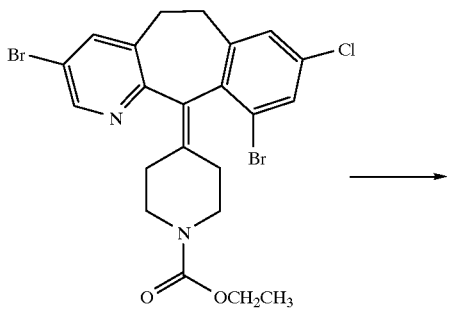

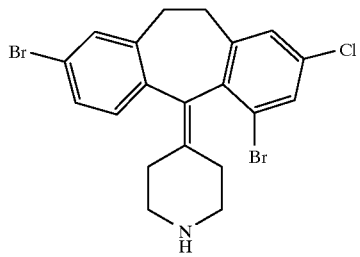

Combine 0.70 g (1.4 mmol) of the product of Step D and 8 mL of concentrated HCI (aqueous) and heat the mixture at reflux overnight. Add 30 mL of 1 N NaOH (aqueous), then 5 mL of 50% NaOH (aqueous) and extract with CH₂Cl₂. Dry the extract over MgSO₄ and concentrate in vacuo to give 0.59 g of the title compound.

PREPARATIVE EXAMPLE 8

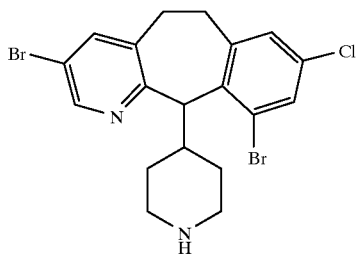

[racemic as well as (+) - and (-) -isomers]

Step A:

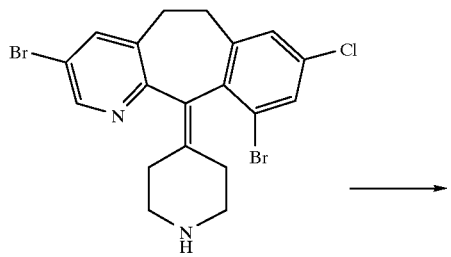

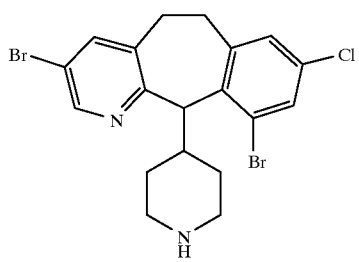

Prepare a solution of 8.1 g of the title compound from Preparative Example 7 in toluene and add 17.3 mL of a 1 M solution of DIBAL in toluene. Heat the mixture at reflux and slowly add (dropwise) another 21 mL of 1 M DIBAL/toluene solution over a period of 40 min. Cool the reaction mixture to about 0° C. and add 700 mL of 1 M HCI (aqueous). Separate and discard the organic phase. Wash the aqueous phase with CH₂Cl₂, discard the extract, then basify the aqueous phase by adding 50% NaOH (aqueous). Extract with CH₂Cl₂, dry the extract over MgSO₄ and concentrate in vacuo to give 7.30 g of the title compound, which is a racemic mixture of enantiomers.

Step B —Separation of Enantiomers:

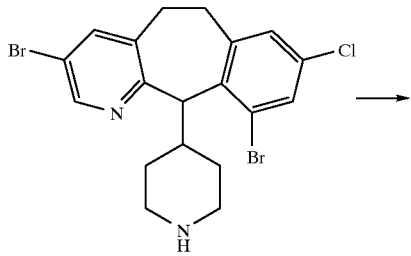

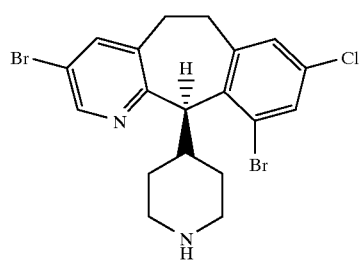

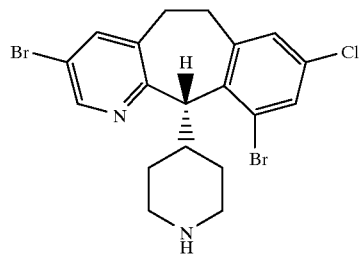

The racemic title compound of Step A is separated by preparative chiral chromatography (Chiralpack AD, 5 cm×50 cm column, using 20% iPrOH/hexane+0.2% diethylamine), to give the (+)-isomer and the (−)-isomer of the title compound.

PREPARATIVE EXAMPLE 48

Step A:

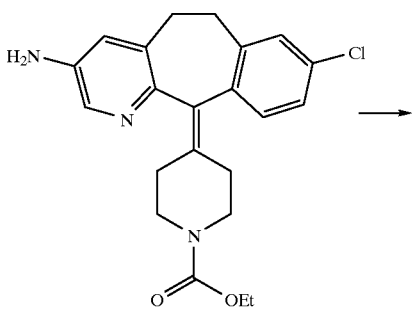

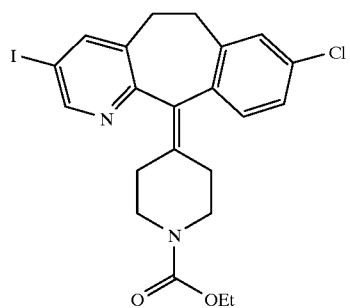

Combine 6 g (15.11 mmol) of the title compound of WO 95/10516's Preparative Example 47B, and benzene, and add 2.3 g (9.06 mmol) of iodine. Heat the mixture at reflux for 3 hours, cool, then dilute with 50 mL of CH₂Cl₂. Wash the organic phase with 5% NaHSO₃ (aqeuous) (3×80 mL), then with 1 M NaOH (aqueous) (2×80 mL), and dry over MgSO₄. Concentrate to a residue chromatograph (silica gel, 30% EtOAc/hexanes), to give 3.2 g (42% yield) of the product iodo compound. Mass Spec.: MH⁺=509

Step B:

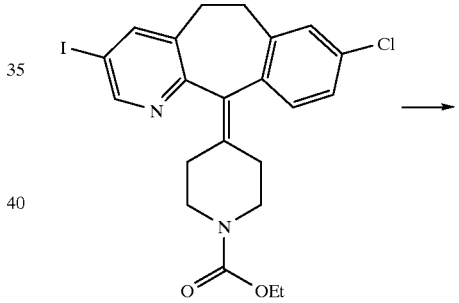

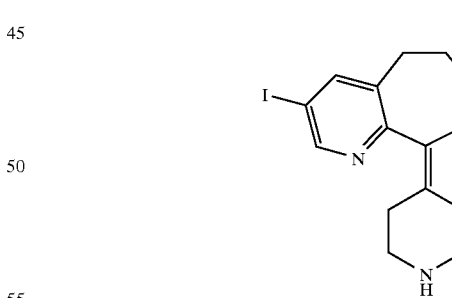

The product of Step A is hydrolyzed via substantially the same procedure as described in Example 358, Step A, of WO 95/10516, to give the iodoamine product in 89% yield.

PREPARATIVE EXAMPLE 49

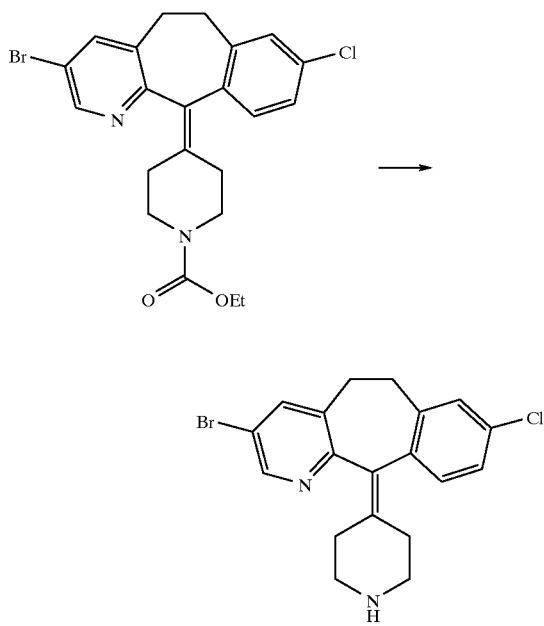

The product of Preparative Example 47, Step C, of WO 95/10516, (2.42 g) is hydrolyzed via substantially the same procedure as described in Example 358, Step A, of WO 95/10516, to give 1.39 g (69% yield) of the bromoamine product.

PREPARATIVE EXAMPLE 51A

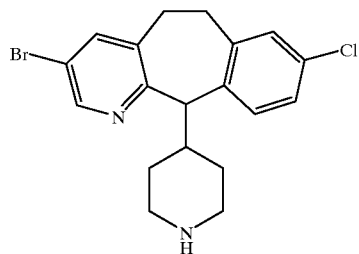

Step A:

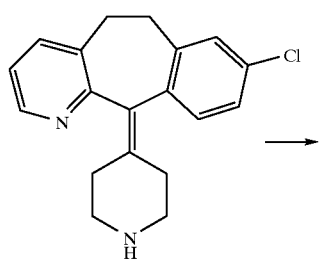

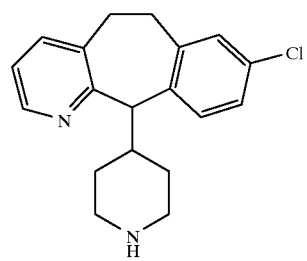

Combine 82.0 g (0.26 mole) of the product of Preparative Example 1, Step G, of WO 95/10516, and 1 L of toluene, then add 20.06 g (0.53 mole) of LiAlH$_4$ and heat the reaction mixture at reflux overnight. Cool the mixture to room temperature and add ~1 L of Et$_2$O, followed by dropwise addition of saturated Na$_2$SO$_4$ (aqueous) until a precipitate forms. Filter and stir the filtrate over MgSO$_4$ for 30 minutes, then concentrate in vacuo to give the product compound in 83% yield. Mass Spec.: MH$^+$=313

Step B:

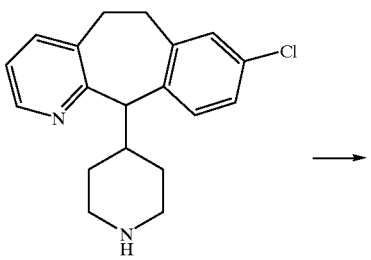

Combine 24.32 g (74.9 mmol) of the Product from Step A, 500 mL of toluene, 83 mL of Et$_3$N and 65.9 mL of ethyl chloroformate and heat the mixture at reflux overnight. Cool to 25° C., pour into 200 mL of water and extract with EtOAc. Dry the extract over MgSO$_4$, concentrate in vacuo to a residue and chromatograph (silica gel, 50% EtOAc/hexane) to give 15 g of the product compound. Mass Spec.: MH$^+$= 385.

Step C:

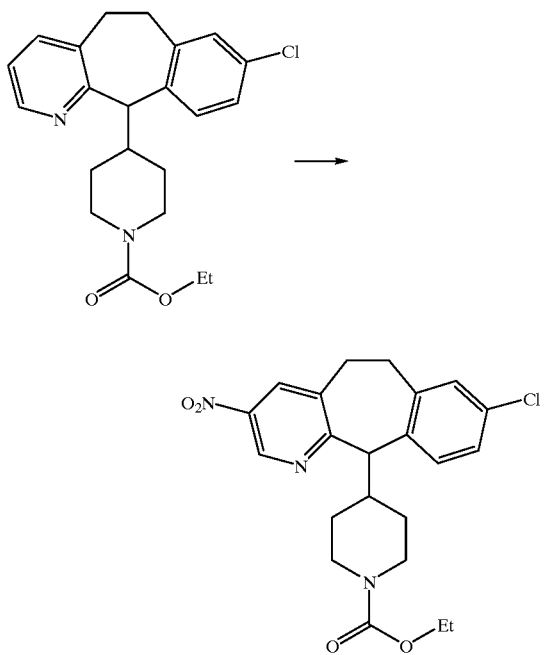

Dissolve 3.2 g (10.51 mmol) of tetra-n-butylammonium nitrate in 25 mL of $CH_2Cl_2$ and add 2.2 g (10.51 mmol, 1.5 mL) of TFAA. Cool to 0° C. and add the mixture (via cannula) to a solution of 3.68 g (9.56 mmol) of the product of Step B in 50 mL of $CH_2Cl_2$ at 0° C., then stir at 00C for 3 hours. Allow the mixture to warm to 25° C. while stirring overnight, then extract with saturated $NaHCO_3$ (aqueous) and dry over $MgSO_4$. Concentrate in vacuo to a residue and chromatograph (silica gel, 30% EtOAc/hexane) to give 1.2 g of the product compound. Mass Spec.: $MH^+$=430

Step D:

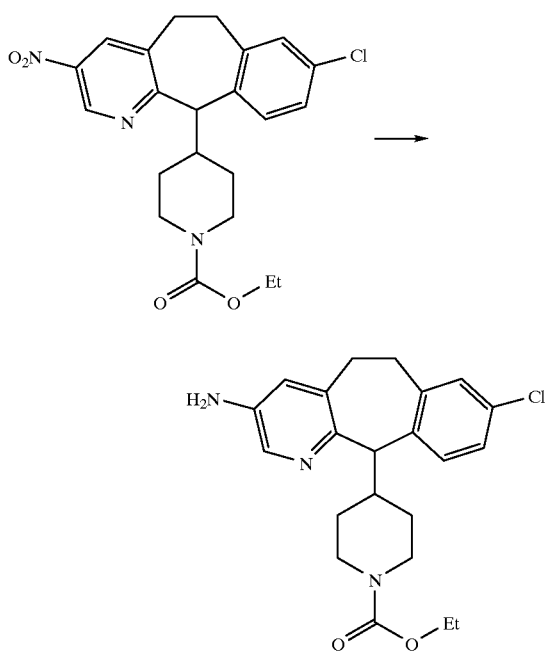

Combine 2.0 g (4.7 mmol) of the Product of Step C and 150 mL of 85% EtOH (aqueous), add 2.4 g (42 mmol) of Fe filings and 0.24 g (2.1 mmol) of $CaCl_2$, and heat at reflux for 16 hours. Filter the hot mixture through a bed of celite®, wash the celite® with hot EtOH. Concentrate the filtrate in vacuo to give a 100% yield of the product compound. Mass Spec.: $MH^+$=400.

Step E:

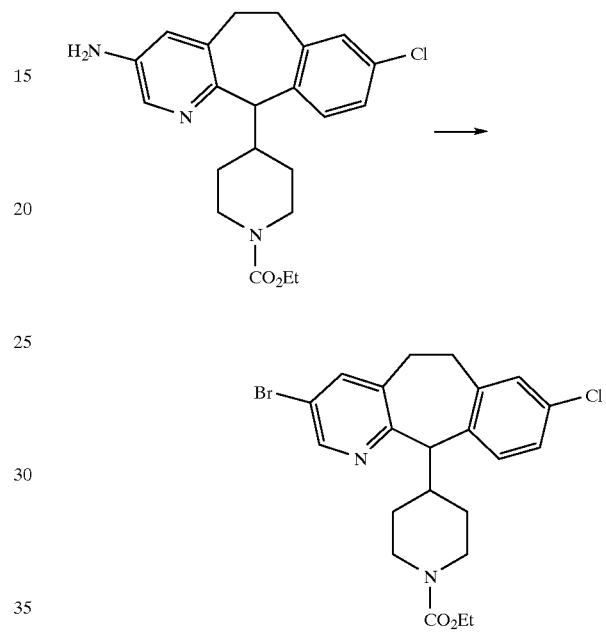

Combine 2.0 g (5.2 mmol) of the Product of Step D and 20 mL of 48% HBr, cool the mixture to −5° C. Stir the mixture at −5° C. for 15 minutes and slowly add a solution of 1.07 g (15.5 mmol) of $NaNO_2$ in 10 mL of water. Stir for 45 minutes, then quench with 50% NaOH (aqueous) to pH ~10. Extract with EtOAc, dry the combined extracts over $MgSO_4$ and concentrate in vacuo to give the product compound. Mass Spec.: $MH^+$=465

Step F:

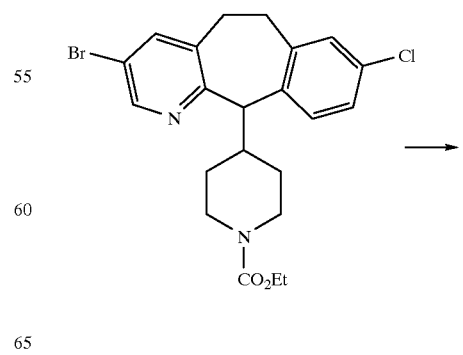

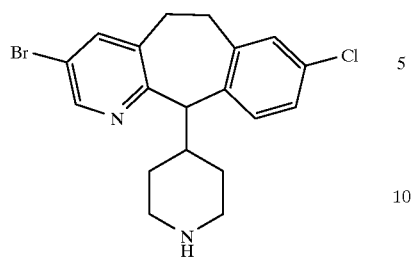

Hydroyze 4.0 g of the Product of Step E via substantially the same process as described for Example 358, Step A, of WO 95/10516, to give 1.39 g of the product compound. Mass Spec.: MH$^+$=392

PREPARATIVE EXAMPLE 53

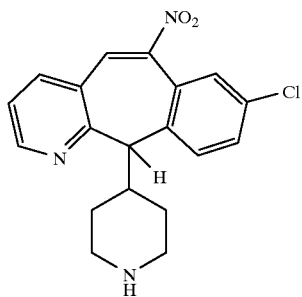

Step A:

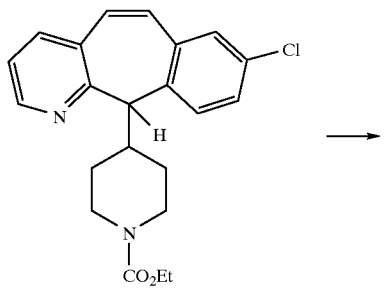

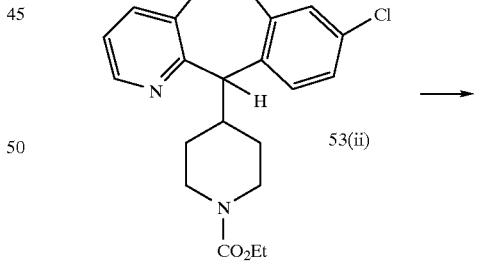

Combine 14.95 g (39 mmol) of the Product of Preparative Example 34A, of WO 95/10516, and 150 mL of $CH_2Cl_2$, then add 13.07 g (42.9 mmol) of $(nBu)_4NNO_3$ and cool the mixture to 0° C. Slowly add (dropwise) a solution of 6.09 mL (42.9 mmol) of TFAA in 20 mL of $CH_2CO_2$ over 1.5 hours. Keep the mixture at 0° C. overnight, then wash successively with saturated $NaHCO_3$ (aqueous), water and brine. Dry the organic solution over $Na_2SO_4$, concentrate in vacuo to a residue and chromatograph the residue (silica gel, EtOAc/hexane gradient) to give 4.32 g and 1.90 g of the two product compounds 53(i) and 53(ii), respectively.

Mass Spec.(53(i)): MH$^+$=428.2; Mass Spec. (53(ii)): MH$^+$=428.3

Step B:

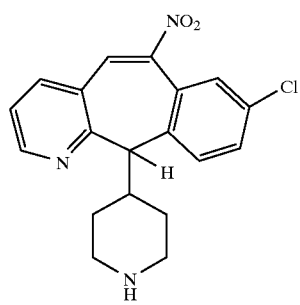

The compound 53(ii) from Step A (0.20 g) is hydrolyzed via substantially the same procedure as described for Example 358, Step A, of WO 95/10516 (published Apr. 20, 1995), to give 0.16 g of the product compound.

Using the starting compound indicated and substantially the same procedure as described in Preparative Example 53, Step B, the compounds in Table 1 are prepared:

TABLE 1

| Starting Compound | Compound | Analytical Data |
|---|---|---|
| Preparative Example 53, Step A, compound 53(i) | Preparative Example 53A | — |
| Preparative Example 54, Step B, compound 54(ii) | Preparative Example 53B | Mass Spec.: MH+ = 466.9 |
| Preparative Example 54, Step B, compound 54(i) | Preparative Example 53C | Mass Spec.: MH+ = 466.9 |

PREPARATIVE EXAMPLE 54

Step A:

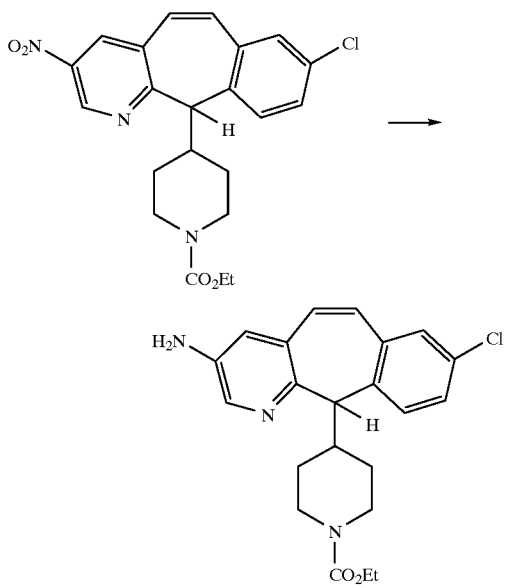

Combine 22.0 g (51.4 mmol) of the product 53(i) from Preparation 53, Step A, 150 mL of 85% EtOH (aqueous), 25.85 g (0.463 mole) of Fe powder and 2.42 g (21.8 mmol) of $CaCl_2$, and heat at reflux overnight. Add 12.4 g (0.222 mole) of Fe powder and 1.2 g (10.8 mmol) of $CaCl_2$ and heat at reflux for 2 hours. Add another 12.4 g (0.222 mole) of Fe powder and 1.2 g (10.8 mmol) of $CaCl_2$ and heat at reflux for 2 hours more. Filter the hot mixture through celite®, wash the celite® with 50 mL of hot EtOH and concentrate the filtrate in vacuo to a residue. Add 100 mL of anhydrous EtOH, concentrate to a residue and chromatograph the residue (silica gel, $MeOH/CH_2Cl_2$ gradient) to give 16.47 g of the product compound.

Step B:

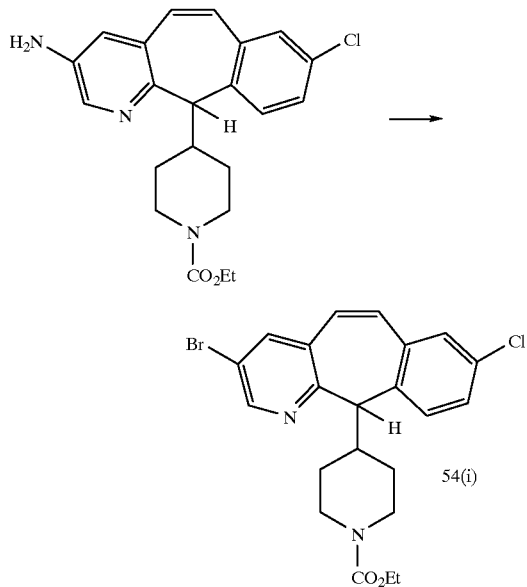

Combine 16.47 g (41.4 mmol) of the product compound from Preparative Example 54, Step A, and 150 mL of 48% HBr (aqueous) and cool to −3° C. Slowly add (dropwise) 18 mL of bromine, then slowly add (dropwise) a solution of 8.55 g (0.124 mole) of $NaNO_{2\beta}$ in 85 mL of water. Stir for 45 minutes at −30° to 0° C., then adjust to pH =10 by adding 50% NaOH (aqueous). Extract with EtOAc, wash the extracts with brine and dry the extracts over $Na_2SO_4$. Concentrate to a residue and chromatograph (silica gel, EtOAc/hexane gradient) to give 10.6 g and 3.28 g of the two product compounds 54(i) and 54(ii), respectively.

Mass Spec. (54(i)): $MH^+$=461.2; Mass Spec. (54(ii)): $MH^+$=539

PREPARATIVE EXAMPLE 55

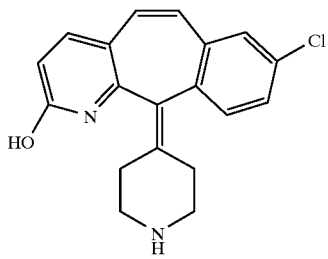

The title compound is known and is prepared by the procedure described in *Bioorg. & Med. Chem. Lett.*, 3, (No. 6) 1073–1078 (1993).

PREPARATIVE EXAMPLE 56

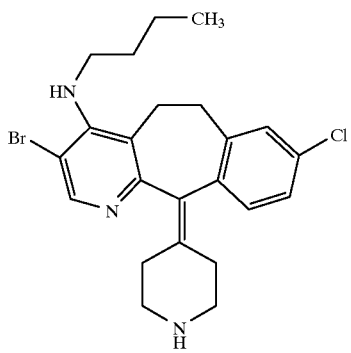

Step A:

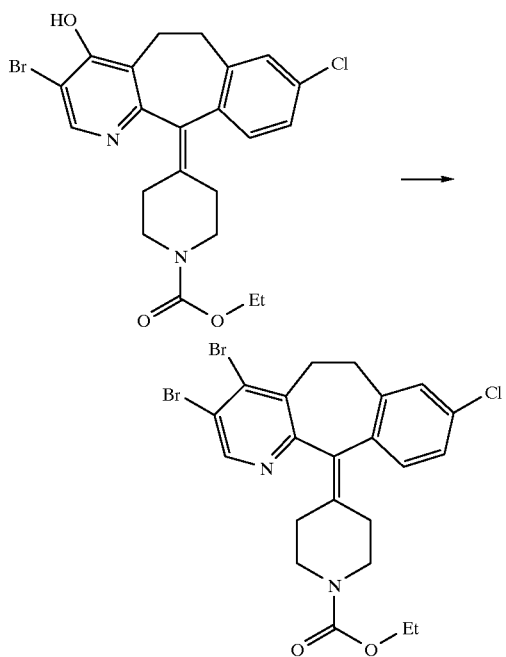

Combine 2.04 g of the product of Preparative Example 44, of WO 95/10516 (published Apr. 20, 1995), 1.3 mL of PBr$_3$, 1.0 mL of Et$_3$N and 20 mL of CH$_2$Br$_2$, and heat the mixture at reflux overnight. Cool the mixture, dilute with CH$_2$Cl$_2$ and wash with 1 N NaOH (aqueous). Dry over MgSO$_4$ and concentrate in vacuo to give 1.22 g (53% yield) of the product compound. Mass Spec.: MH$^+$=541

Step B:

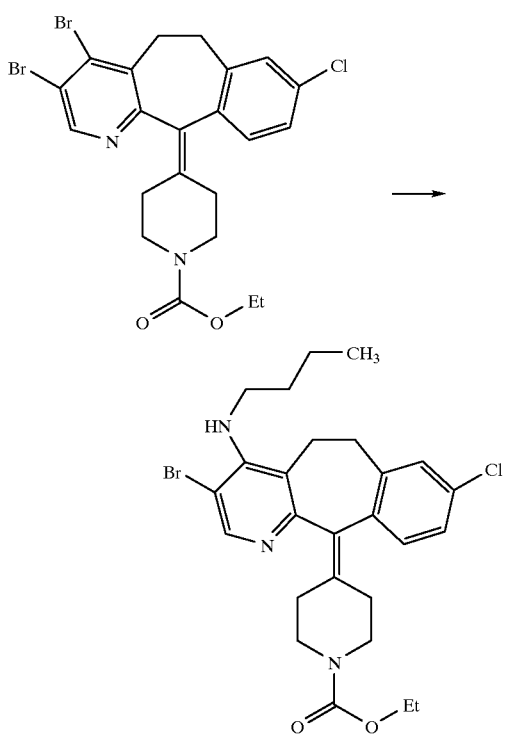

Combine 0.3 g of the product compound from Preparative Example 56, Step A, and 8 mL of n-butylamine and stir at 120° C. in a sealed tube for 48 hours. Concentrate in vacuo to a residue and purify by preparative plate chromatography (silica gel, 1.5–2.5% MeOH/CH$_2$Cl$_2$) to give 80 mg (27%) yield of the product compound. Mass Spec.: MH$^+$=534

Step C:

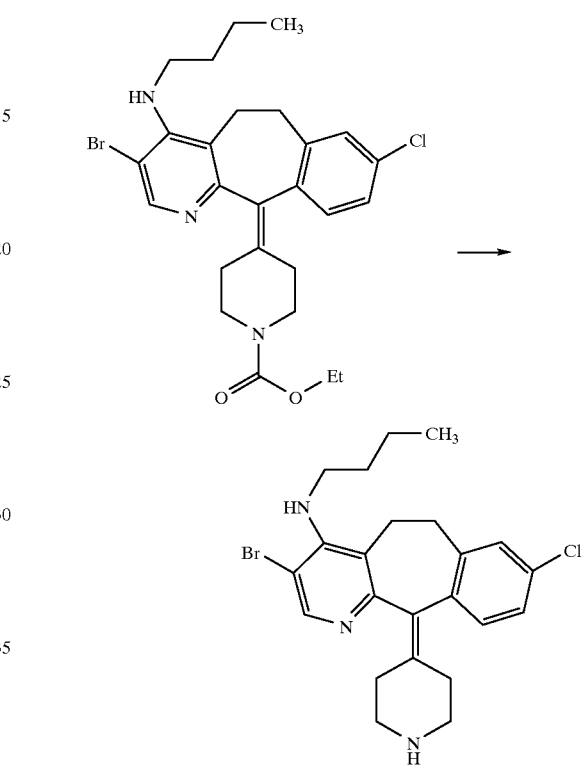

Combine 66 mg of the product compound from Preparative Example 56, Step B, 4 mL of anhydrous EtOH, and 15 mL of concentrated HCl stir at reflux for 60 hours. Cool the reaction mixture to about 0° C. and basify by adding KOH. Extract with CH$_2$Cl$_2$, dry the extract over MgSO$_4$, and concentrate in vacuo to give 46 mg (81 % yield) of the product compound. Mass Spec.: MH$^+$=462

PREPARATIVE EXAMPLE 57

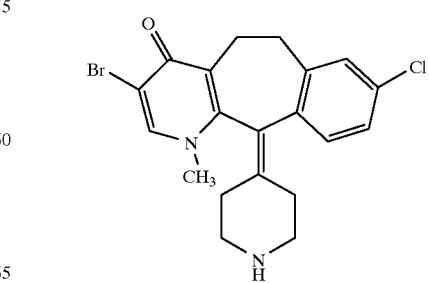

Step A:

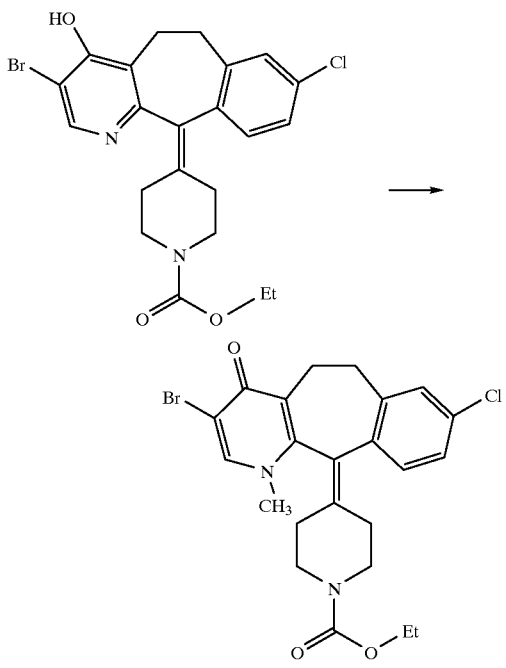

Combine 1.19 g of the product of Preparative Example 44, of WO 95/10516, 10 mL of anhydrous DMF, 0.2 g of NaH (60% in mineral oil) and 0.19 mL of methyl iodide, and stir at room temperature overnight. Concentrate in vacuo to a residue, dilute the residue with $CH_2Cl_2$, wash with saturated $NaHCO_3$ (aqueous), and dry over $MgSO_4$. Concentrate in vacuo to give 1.13 g (92% yield) of the product compound. Mass Spec.: $MH^+$=493.

Step B:

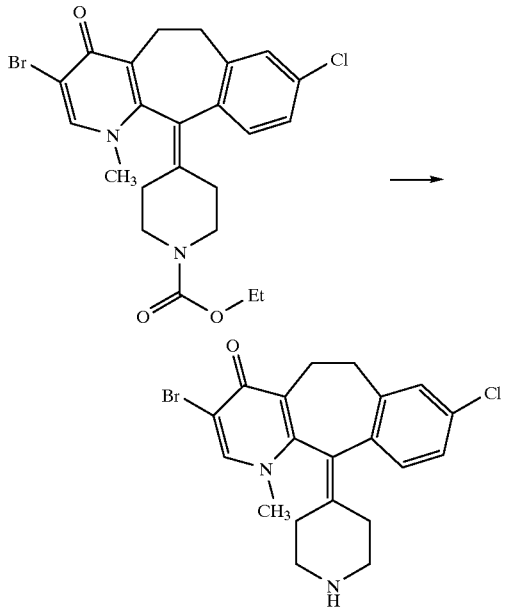

Hydrolyze 1.13 g of the product of Step A via substantially the same procedure as described for Preparative Example 56, Step C, to give 0.61 g (63% yield) of the product compound.

PREPARATIVE EXAMPLE 58

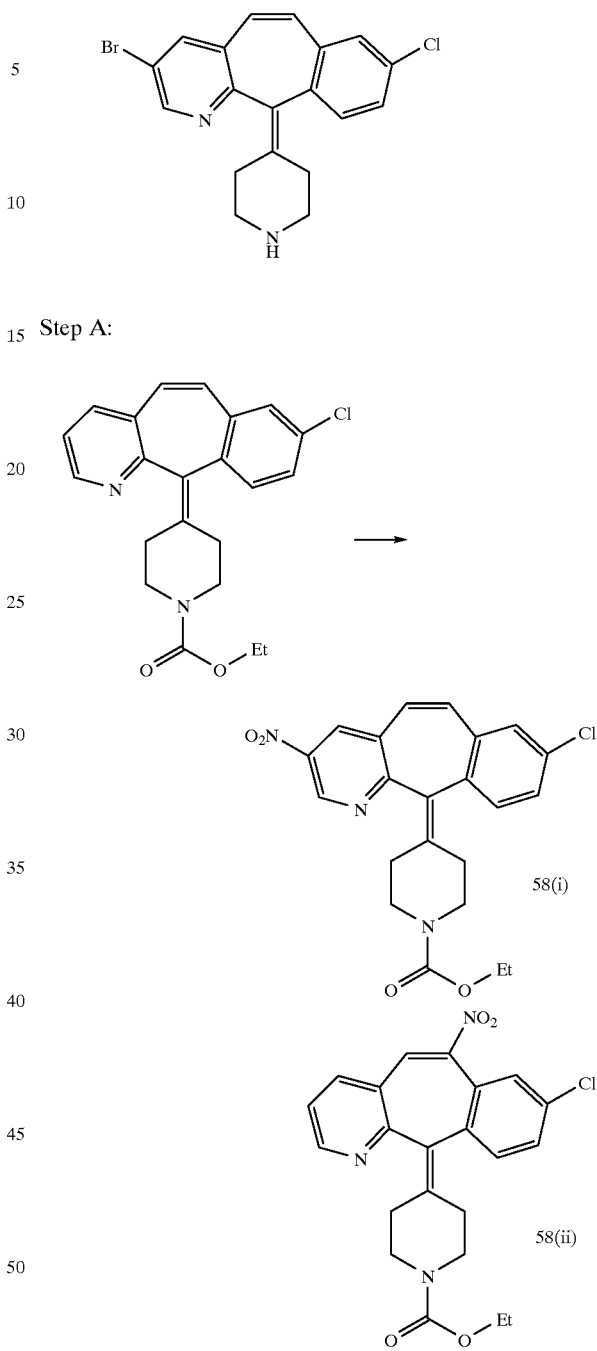

Step A:

Combine 1.07 g (3.52 mmol) of tetrabutylammonium nitrate, 4 mL of anhydrous $CH_2Cl_2$ and 0.743 g (3.52 mmol) of TFAA, and add the resulting mixture to a solution of 1.22 g (3.20 mmol) of the title compound of Preparative Example 37, of WO 95/10516, in 8 mL of anhydrous $CH_2Cl_2$ at room temperature. Stir at room temperature overnight, then wash with 20 mL of saturated $NaHCO_3$ (aqueous) and 20 mL of brine, and dry over $MgSO_4$. Concentrate in vacuo and chromatograph the resulting residue (silica gel, EtOAc/ hexane) to give 0.216 g of the product compound 58(i) and 0.27 g of the product compound 58(ii). Mass Spec. (58(i)): $MH^+$=426. m.p. (58(i)) 97.5°–99.2° C.

Step B:

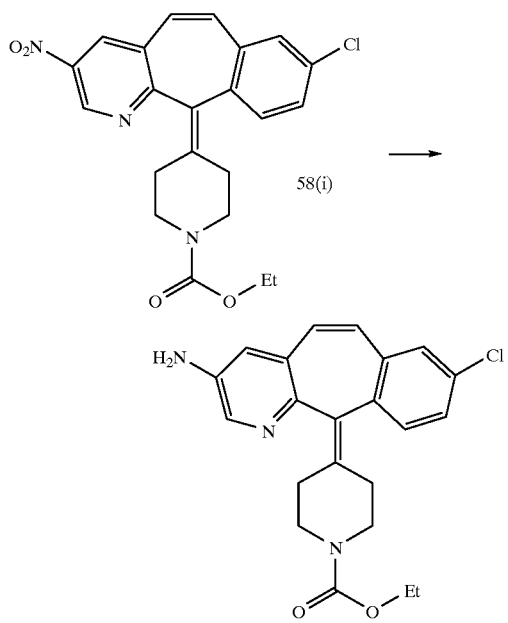

Reduce the product 58(i) from Step A via essentially the same procedure as described in Preparative Example 47, Step B, of WO 95/10516, to give the product compound. Mass Spec.: MH⁺=396

Step C:

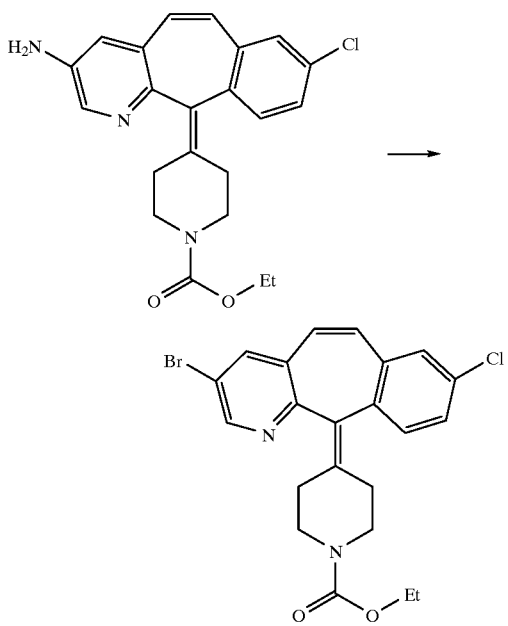

React the product from Step B with HBr and bromine via essentially the same procedure as described in Preparative Example 47, Step C, of WO 95/10516, to give the product compound. Mass Spec.: MH⁺=459

Step D:

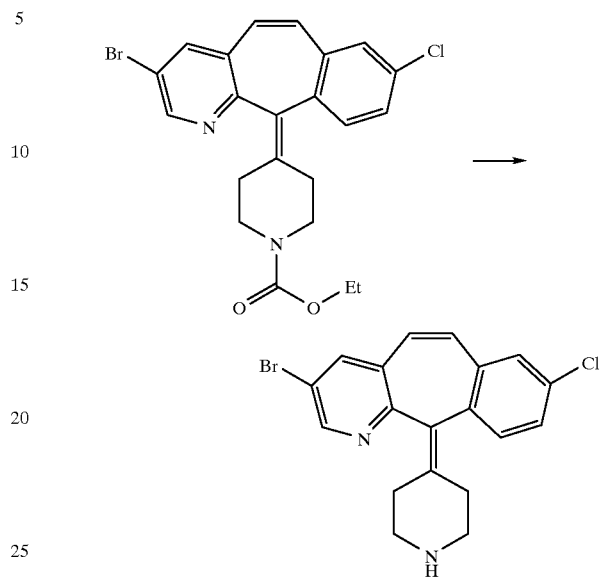

Hydrolyze 0.83 g of the product from Step C via essentially the same procedure as described in Preparative Example 56, Step C, to give 0.56 g of the product compound. Mass Spec.: MH⁺=387

PREPARATIVE EXAMPLE 60

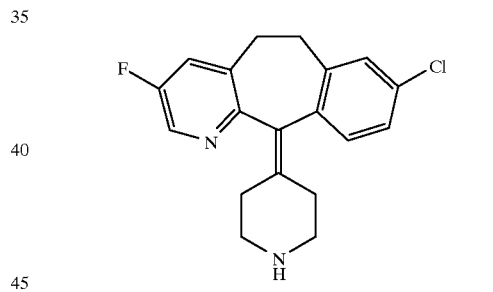

Step A:

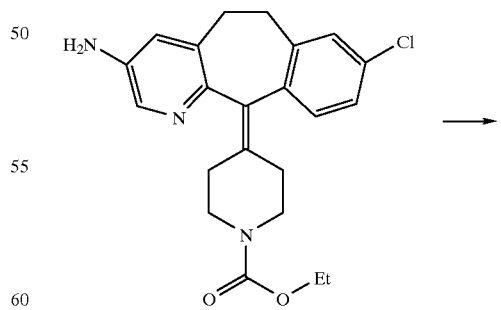

-continued

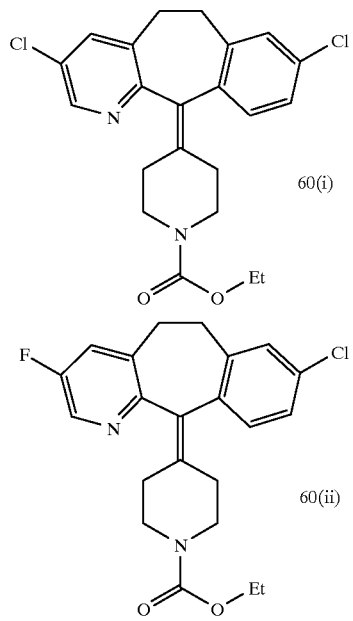

Combine 16.25 g (40.83 mmol) of the product of Preparative Example 47, Step B. of WO 95/10516, and a slurry of 7.14 g (61.11 mmol) of NOBF$_4$ in 100 mL of CH$_2$Cl$_2$ and stir the mixture for 3 hours. Add 100 mL of o-dichlorobenzene and heat for 5 hours, distilling the CH$_2$Cl$_2$ from the mixture. Concentrate in vacuo to a residue, add 200 mL of CH$_2$Cl$_2$ and wash with water (2×200 mL). Dry over MgSO$_4$, concentrate in vacuo to a residue, and chromatograph (silica gel, 20% EtOAc/hexane) to give 4.1 g of product compound 60(i) and 4.01 g of Product compound 60(ii). Mass Spec. (60(i)): MH$^+$=418. MassSpec.(60(ii)): MH$^+$=401
Step B:

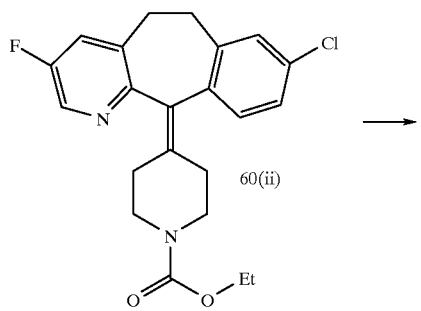

Hydrolyze 3.4 g of the product 60 (ii) from Step A via essentially the same process as described for Example 358, Step A, of WO 95/10516, to give 3.01 g of product compound. Mass Spec.: MH$^+$=329

Using compound 60(i) from Preparative Example 60, Step A, and following substantially the same procedure as described in Preparative Example 60, Step B, the compound:

(Preparative Example 60A)

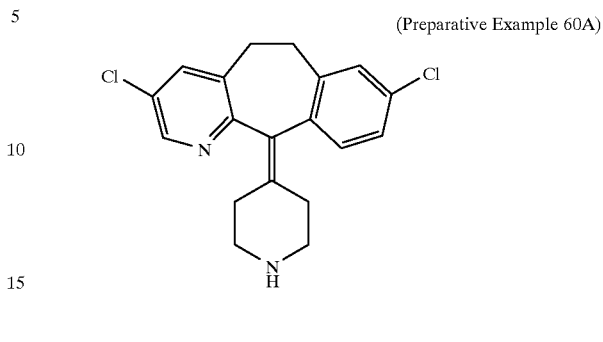

was prepared. Mass Spec.: MH$^+$=346.

PREPARATIVE EXAMPLE 66

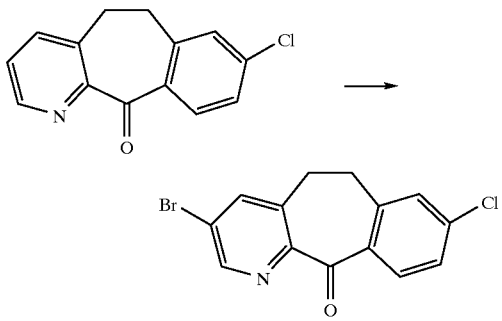

Cool 50.0 g (20.5 mmol) of 8-chloro-5,6-dihydro-11H-benzo[5,6]cyclohepta[1,2-b]pyridin-11-one to 0° C., slowly add 75 mL (93.69 mmol) of sulfur monochloride over 20 minutes, then slowly add 25 mL (48.59 mmol) of Br$_2$ over 15. Heat at 95° C. for 20 hour, add 12.5 mL (24.3 mmol) of Br$_2$ and heat for a another 24 hours. Cool the mixture, and slowly add to a mixture of CH$_2$Cl$_2$ and 1 N NaOH (aqueous) at 0° C. Wash the organic phase with water, dry over MgSO$_4$ and concentrate in vacuo to a residue. Chromatograph the residue (silica gel, 500 mL CH$_2$Cl$_2$ then 0.2%–5% (10% NH$_4$OH in MeOH)/CH$_2$Cl$_2$), then chromatograph again (silica gel, 3%–8.5% EtOAc/hexane) to give 8.66 g of the product compound. Mass Spec.: MH$^+$=322

PREPARATIVE EXAMPLE 67

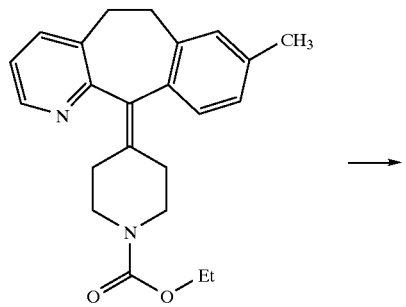

-continued

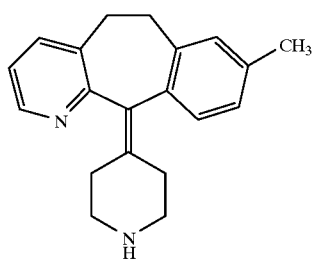

Dissolve 0.16 g (0.46 mmol) of 4-(8-methyl-5,6-dihydro-11H-benzo[5,6]cyclohepta[1,2-b]pyridin-11-ylidine)-1-ethoxycarbonyl-piperidine, in 2 mL EtOH and add 4 mL of 12 N HCl. Heat the solution for 3 hours at 85° C., then cool to 25° C. Adjust to pH =10 with 50% NaOH a (aqueous) and extract several times with 50 mL of EtOAc. Combine the organic layers, dry them over MgSO$_4$, and concentrate in vacuo to give the product compound.

PREPARATIVE EXAMPLE 68

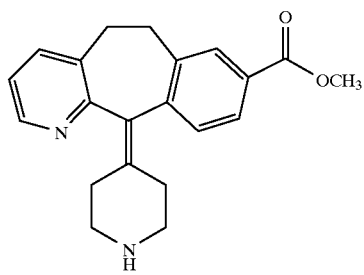

Step A:

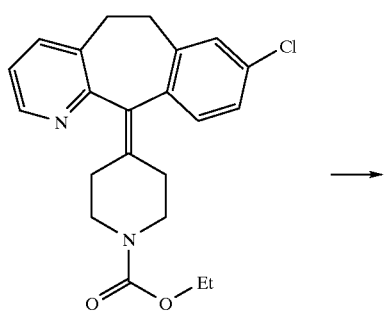

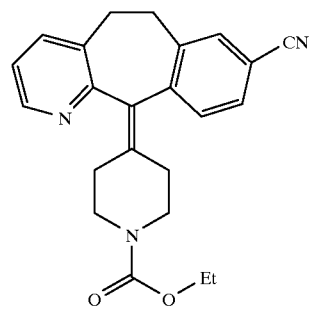

Disolve 2 g (5.22 mmol) of the title compound of Preparative Example 1 F, of WO 95/10516, in 2.6 mL of dry N-methylpyrrolidinone. Add 0.87 g (9.4 mmol) of CuCN and 0.139 g (0.93 mmol) of sodium iodide. Heat the mixture at 200° C. under nitrogen for 20 hours, cool to 25° C. and repeatedly grind and mix with five 50 mL portions of CH$_2$Cl$_2$ and 7M NH$_4$OH (aqueous). Wash the organic layer with 7M NH$_4$OH until the organic layer is no longer blue or green. Dry the combined organic layers over MgSO$_4$ and concentrate in vacuo to a residue. Chromatograph (silica gel 70% EtOAc/hexane), then recrystallize from EtOAc/hexane to give the product compound. m.p.=152.4°–153.5° C.; Mass Spec.: MH$^+$=374

Step B:

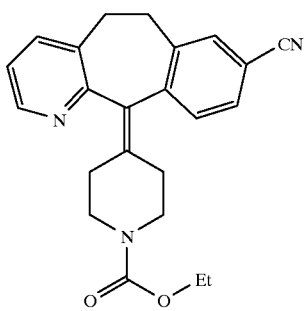

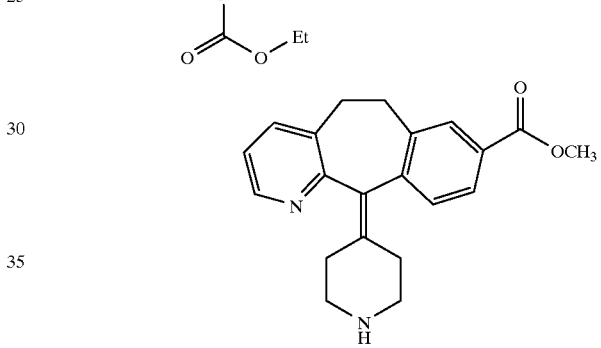

Dissolve 4.08 g (10.93 mmol) of the product of Step A in 12M HCl and heat at 85° C. for 18 hours. Concentrate in vacuo to a residue. Dissolve the residue in 175 mL of MeOH, saturate with HCl gas, and heat at reflux for 18 hours. Concentrate in vacuo to give the product compound as its HCl salt. Mass Spec.: MH$^+$=335

PREPARATIVE EXAMPLE 69

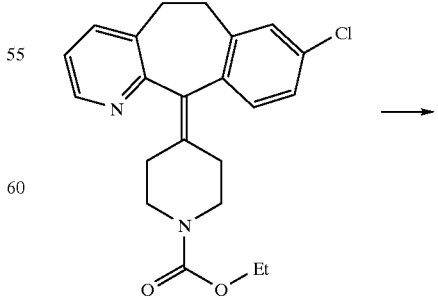

83
-continued

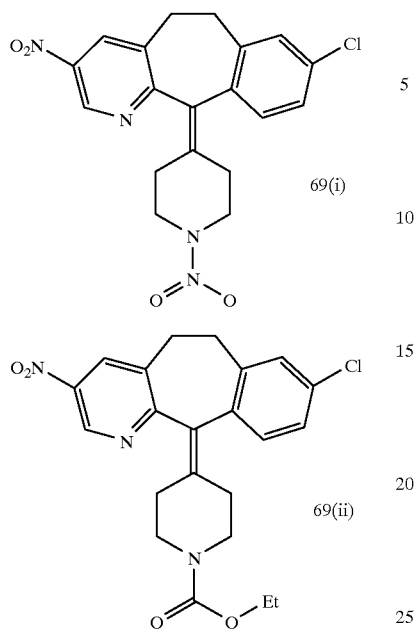

Combine 75 g (0.196 mole) of the Product of Example 1, Step F, of WO 95/10516, and 300 mL of CH$_2$Cl$_2$ at 0° C., and slowly add (dropwise) a solution of 72 g (0.236 mole) of tetrabutylammonium nitrate and 35 mL (0.247 mole) of TFAA in 500 mL of CH$_2$Cl$_2$. Stir at 25° C. overnight, slowly add (dropwise) 1 L of saturated NaHCO$_3$ (aqueous). Separate the layers, wash the organic phase with brine and dry over MgSO$_4$. Concentrate in vacuo to a residue, chromatograph twice (1 kg silica gel, gradient of EtOAc/CH$_2$Cl$_2$) to give 8.63 g of product compound 69(i), and 34 g of product compound (ii). Recrystallize compound 69(i) from CH$_2$Cl$_2$/hexane to give the purified product compound 69(i). m.p.= 186°–187° C.; Mass Spec.: (FAB) MH$^+$=401

PREPARATIVE EXAMPLE 69A

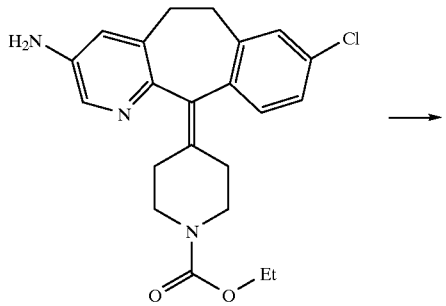

84
-continued

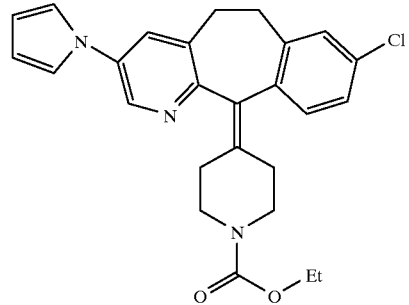

Combine 0.4 g (1 mmol) of the Product of Example 47, Step B, of WO 95/10516 (published Apr. 20, 1995), and 0.2 mL (1.2 mmoles) of 2,5-diethoxytetrahydrofuran in 3 mL of glacial HOAc, and heat at reflux for 1.5 hours. Cool the mixture, wash with saturated NaHCO$_3$ (aqueous), then with brine, dry over MgSO$_4$, and concentrate in vacuo to a residue. Chromatograph (silica gel, 5%–15% EtOAc/CH$_2$Cl$_2$) to give 0.34 g of the product compound. Mass Spec.: (FAB) MH$^+$=448

PREPARATIVE EXAMPLE 70

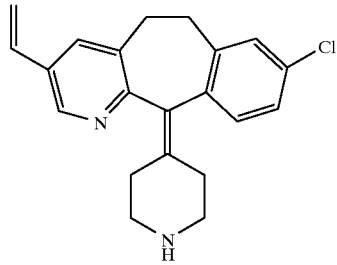

Step A:

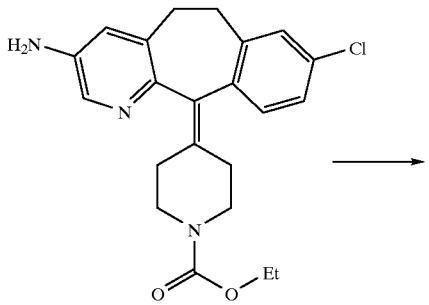

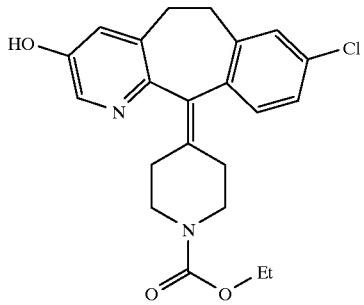

Combine 13.8 g (34.7 mmol) of the Product of Example 47, Step B, of WO 95/10516, and 90 mL of water at 0° C., add a solution of 6.9 mL of concentrated $H_2SO_4$ in 45 mL of water and stir the mixture. Slowly add (dropwise) a solution of 2.55 g (40 mmol) of $NaNO_2$ in 75 mL of water and stir at 0°–5° C. for 0.5 hours. Add a boiling solution of 35.1 g $CuSO_4$ in 135 mL of water and heat at 100° C. for 15 min. Cool the mixture, extract with $CH_2Cl_2$ (2×200 mL), wash the extracts with brine, dry over $MgSO_4$, and concentrate in vacuo to a residue. Chromatograph (silica gel, 1.5%–10% $MeOH/CH_2Cl_2$) to give 11.36 g of the product compound.

Step B:

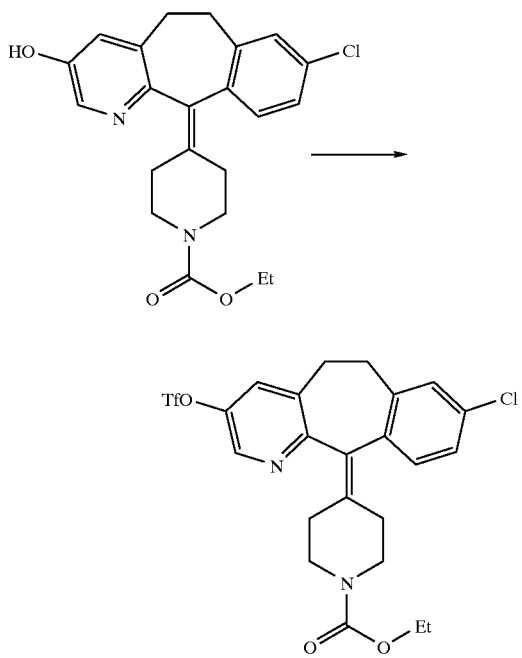

Combine 11.36 g (28.5 mmol) of the Product of Step A and 12.4 g (34.7 mmol) of N—phenyltriflimide in 120 mL of dry $CH_2Cl_2$ at 0° C., add 4.6 mL (33 mmol) of $Et_3N$ and stir at 25° C. overnight. Concentrate in vacuo to a residue and chromatograph (silica gel, 2%–5% EtOAc/ $CH_2Cl_2$) to give 10.95 g of the product compound. Recrystallize from hot MeOH. m.p.=154.5°–156° C.; Mass Spec.: (FAB) $MH^+$=531

Step C:

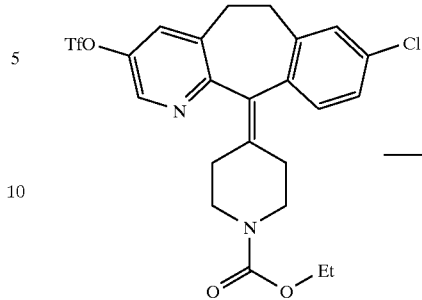

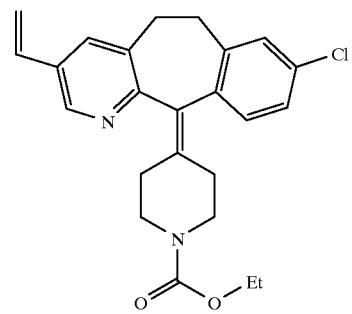

Combine 12.2 g (23 mmol) of the Product of Step B and 85 mL of 1-methyl-2-pyrrolidinone at 25° C., then add 2.84 g LiCl, 0.212 g of tris-furylphosphine and 0.585 g of dipalladiumtribenzylideneacetone and stir for 15 min. Slowly add (dropwise) 7.5 mL (25.77 mmol) of tributylvinyltin and stir at 25° C. for 2.5 hours. Dilute with 500 mL of water at 0° C. and extract with 6700 mL of EtOAc. Filter the organic phase through celite®, wash the celite with EtOAc, then wash the filtrate twice with 30% NaF (aqueous). Filter the organic solution, wash with brine and dry over $MgSO_4$. Concentrate in vacuo to a residue and chromatograph (silica gel, 15%–40% EtOAc/hexane) to give 8.58 g of the product compound. Mass Spec.: (FAB) $MH^+$=409

Using 2-(tributylstannyl)thiophene and the compound of Preparative Example 70, Step B, and following substantially the same procedure as described for Preparative Example 70, Step C, the compound:

(Preparative Example 70-A)

was prepared. m.p.=155°–157° C., Mass Spec.: $MH^+$=465.

Step D:

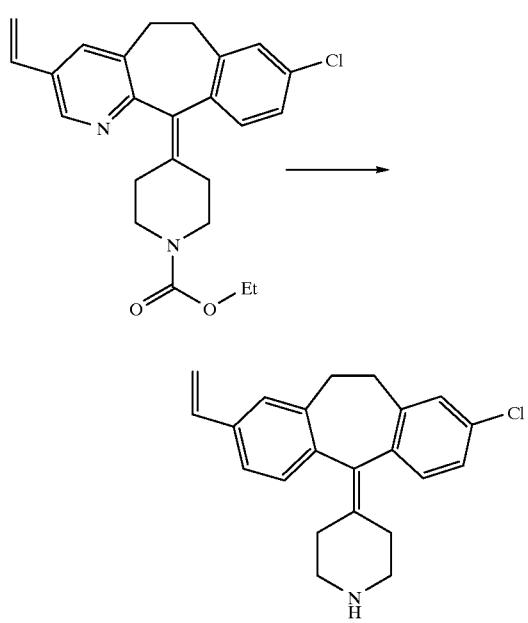

Hydrolyze 1.18 g (2.89 mmol) of the product of Step C via substantially the same procedure as described in Example 358, Step A, of WO 95/10516, to give 0.95 g of the product compound. Mass Spec.: (FAB) MH⁺=337

PREPARATIVE EXAMPLE 71

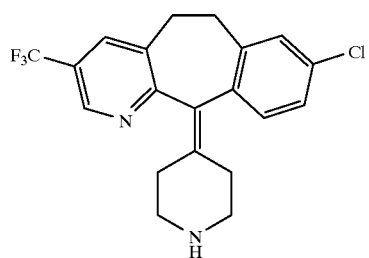

Step A:

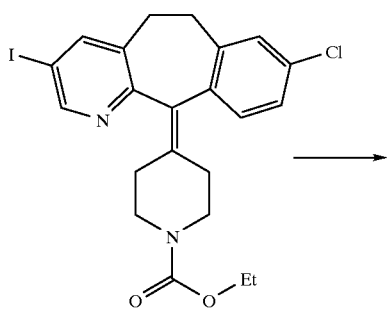

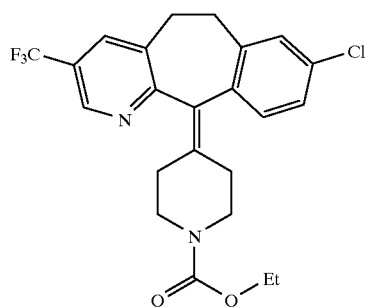

Combine 1.01 g (19.9 mmol) of the Product of Preparative Example 48, Step A, 30 mL of DMF, 1.33 g (6.96 mmol) of methyl 2,2-difluoro-2-(fluorosulfonyl)-acetate and 0.75 g (3.97 g) of CuI. Heat the mixture at 60°–80° C. for 3 hours, then concentrate to a residue. Dilute the residue with water, extract with $CH_2Cl_2$, and concentrate in vacuo to a residue. Chromatograph (silica gel, 30% EtOAc/hexane, then 10% MeOH/$CH_2Cl_2$+NH₄OH) to give 0.15 g of the product compound. Mass Spec.: MH⁺=451.1

Step B:

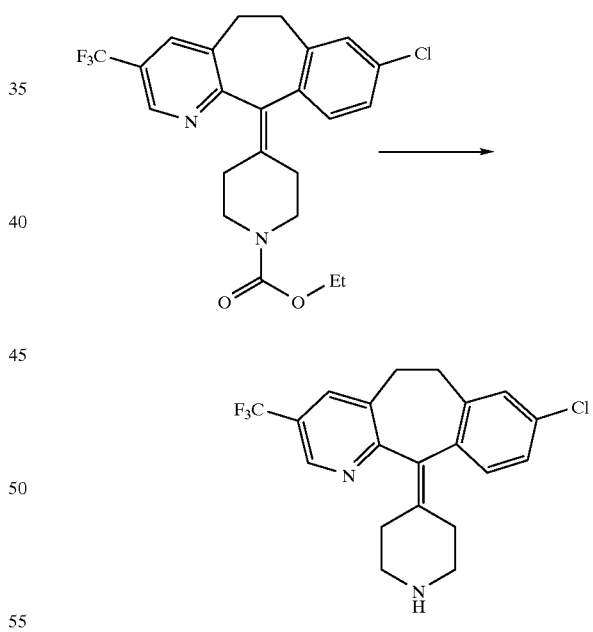

Hydrolyze the product of Step A using essentially the same procedure as described in Preparative Example 1, Step G, of WO 95/10516, to give the product compound. Mass Spec.: MH⁺=379

PREPARATIVE EXAMPLE 72

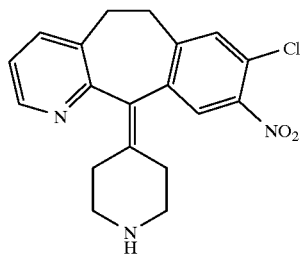

Step A:

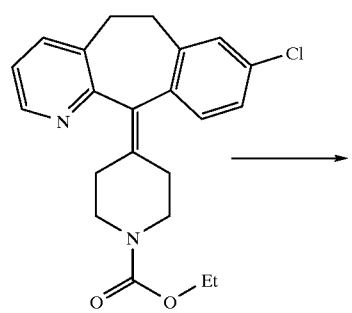

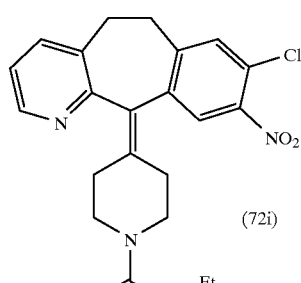

+

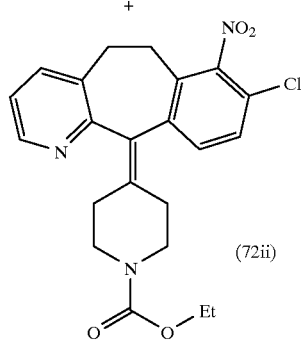

Dissolve 20 g (50 mmol) of the Product of Preparative Example 1, Step F, of WO 95/10516, in 400 mL of concentrated $H_2SO_4$, cool to −5° C. and add 5.1 g (50 mmol) of $KNO_3$ in small portions. Stir for 3 hours, cool the mixture and slowly basify with 50% NaOH (aqueous). Extract with $CH_2Cl_2$ (3×500 ML), dry the combined extracts over $MgSO_4$, and concentrate in vacuc to a residue. Chromatograph (silica gel, 50% EtOAc/hexane) to give 16.33 g of the product compound (72i) and 2.6 g of the product compound (72ii). Mass Spec. (72(i) and (72(ii)): $MH^+=428$ Step B:

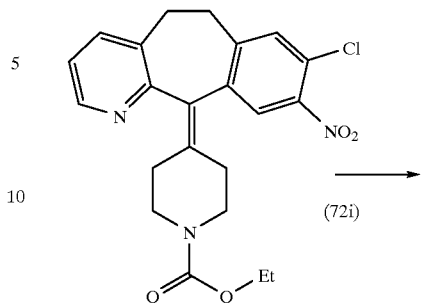

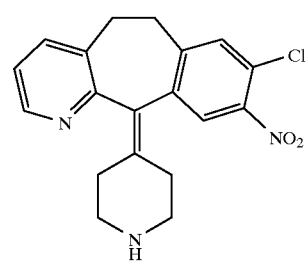

Hydrolyze 5.46 g (12.76 mmol) of the Product of (72i) from Step A, via substantially the same procdure as described for Example 358, Step A, of WO 95/10516, to give 4.34 g of the product compound. Mass Spec.: $MH^+=356$

PREPARATIVE EXAMPLE 73

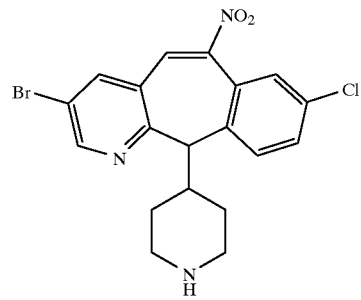

Step A:

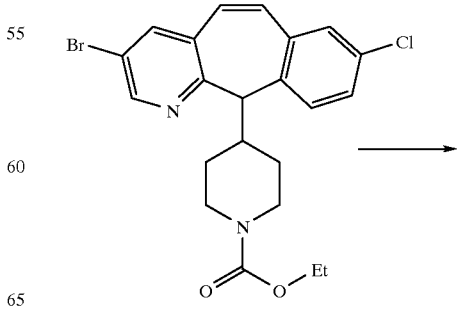

-continued

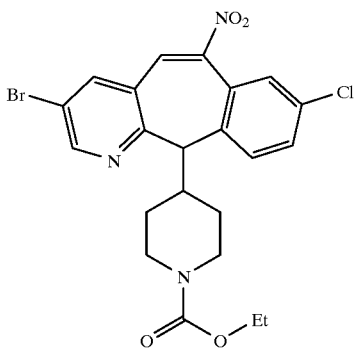

Combine 1.6 g of the Product (54i) of Preparative Example 54, Step B, 12 mL of $CH_2Cl_2$, and 1.16 g of tetrabutylammonium nitrate, cool to 0° C. and slowly add (dropwise) a solution of 0.8 g of TFAA in 2 mL of $CH_2Cl_2$. Stir for 6 hours at 0° C., let the mixture stand at 0° C. overnight, then wash successively with saturated $NaHCO_3$ (aqueous), water and brine, and dry over $Na_2SO_4$. Concentrate in vacuo to a residue, then chromatograph (silica gel, 30% EtOAc/hexane) to give 0.38 g of the product compound.

Step B:

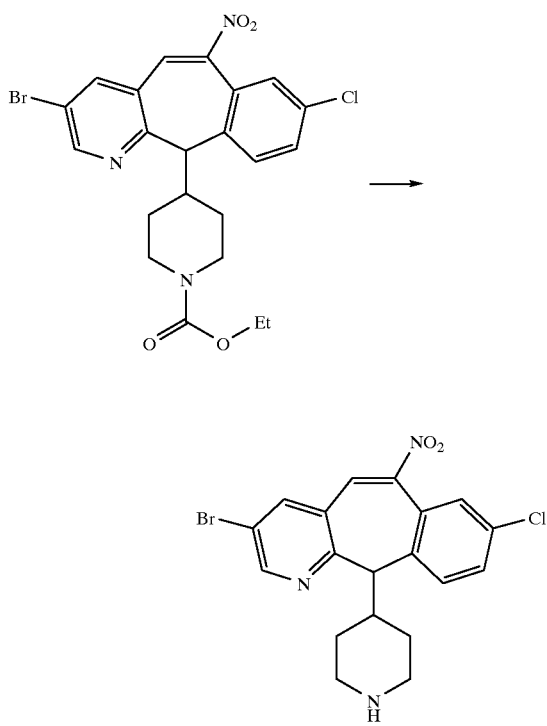

Hydrolyze 0.38 g of the Product of Step A via substantially the same procedure as described for Example 358, Step A, of WO 95/10516, to give 0.235 g of the product compound.

PREPARATIVE EXAMPLE 75

4-(3-bromo-8-chloro-5,6-dihydro-11H-benzo[5.6]cyclohepta[1,2-b]pyridin-11-ylidene)-N-(4H-1,3-benzodioxin-6-yl)-1-piperidinecarbothioamide

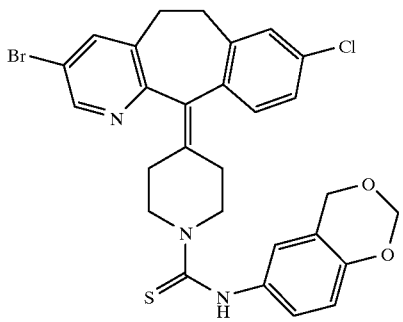

Dissolve 4-(3-bromo-8-chloro-5,6-dihydro-11H-benzo[5.6]cyclohepta[1,2-b]pyridin-11-ylidene)-1-piperidine (0.5 gm, 1.61 mmol) in 5 mL of dry tetrahydrofuran. Add 4H-1,3-benzodioxin-6-yl) isothiocyanate (0.34 gm, 1.77 mmol) and stir at ambient temperature for 24 hours. Evaporate the reaction mixture to an oil and chromatograph on silica gel using 1% up to 5% methanol/methylene chloride as the eluent to obtain 0.893 g of title compound. FABMS M+1= 694

ASSAYS

1. In vitro enzyme assays: FPT $IC_{50}$ (inhibition of farnesyl protein transferase, in vitro enzyme assay) are determined by the methods disclosed in WO/10515 or WO 95/10516. The data demonstrate that the compounds of the invention are inhibitors of Ras-CVLS farnesylation by partially purified rat brain farnesyl protein transferase (FPT). The data also show that there are compounds of the invention which can be considered as potent ($IC_{50}$<10 $\mu$M) inhibitors of Ras-CVLS farnesylation by partially purified rat brain FPT.

2. Cell-based assay. COS $IC_{50}$ values refer to the COS cells activity inhibition of Ras processing, are determined by the methods disclosed in WO/10515 or WO 95/10516.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art, e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound in a unit dose of preparation may be varied or adjusted from about 0.1 mg to 1000 mg, more preferably from about 1 mg. to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of the invention and the pharmaceutically acceptable salts thereof will be regulated according to the judgment of the attending clinician considering such factors as age, condition and size of the patient as well as severity of the symptoms being treated. A typical recommended dosage regimen is oral administration of from 10 mg to 2000 mg/day preferably 10 to 1000 mg/day, in two to four divided doses to block tumor growth. The compounds are non-toxic when administered within this dosage range.

The following are examples of pharmaceutical dosage forms which contain a compound of the invention. The scope of the invention in its pharmaceutical composition aspect is not to be limited by the examples provided.

Pharmaceutical Dosage Form Examples

EXAMPLE A-Tablets

| No. | Ingredients | mg/tablet | mg/tablet |
|---|---|---|---|
| 1. | Active compound | 100 | 500 |
| 2. | Lactose USP | 122 | 113 |
| 3. | Corn Starch, Food Grade, as a 10% paste in Purified Water | 30 | 40 |
| 4. | Corn Starch; Food Grade | 45 | 40 |
| 5. | Magnesium Stearate | 3 | 7 |
| | Total | 300 | 700 |

Method of Manufacture

Mix Item Nos. 1 and 2 in a suitable mixer for 10–15 minutes. Granulate the mixture with Item No. 3. Mill the damp granules through a coarse screen (e.g., ¼", 0.63 cm) if necessary. Dry the damp granules. Screen the dried granules if necessary and mix with Item No. 4 and mix for 10–15 minutes. Add Item No. 5 and mix for 1–3 minutes. Compress the mixture to appropriate size and weigh on a suitable tablet machine.

EXAMPLE B-Capsules

| No. | Ingredient | mg/capsule | mg/capsule |
|---|---|---|---|
| 1. | Active compound | 100 | 500 |
| 2. | Lactose USP | 106 | 123 |
| 3. | Corn Starch, Food Grade | 40 | 70 |
| 4. | Magnesium Stearate NF | 7 | 7 |
| | Total | 253 | 700 |

Method of Manufacture

Mix Item Nos. 1, 2 and 3 in a suitable blender for 10–15 minutes. Add Item No. 4 and mix for 1–3 minutes. Fill the mixture into suitable two-piece hard gelatin capsules on a suitable encapsulating machine.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

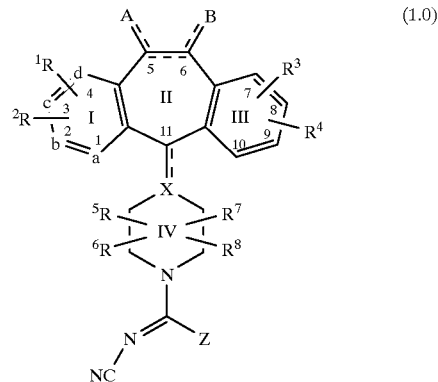

or a pharmaceutically acceptable salt or solvate thereof, wherein:

one of a, b, c and d represents N or $NR^9$ wherein $R^9$ is $O^{31}$, $-CH_3$ or $-(CH2)_nCO_2H$ wherein n is 1 to 3, and the remaining a, b, c and d groups represent $CR^1$ or $CR^2$; or each of a, b, c, and d are independently selected from $CR^1$ or $CR^2$; each $R^1$ and each $R^2$ is independently selected from H, halo, $-CF_3$, $-OR^{10}$, $-COR^{10}$, $-SR^{10}$, $-S(O)_tR^{11}$ (wherein t is 0, 1 or 2) $-SCN$, $-N(R^{10})_2$, $-NR^{10}R^{11}$, $-NO_2$, $-OC(O)R^{10}$, $-CO_2R^{10}$, $-OCO_2R^{11}$, $-CN$, $-NHC(O)R^{10}$, $-NHSO_2R^{10}$, $-CONHR^{10}$, $-CONHCH_2CH_2OH$, $-NR^{10}COOR^{11}$, $-SR^{11}C(O)OR^{11}$, $-SR^{11}N(R^{75})_2$ wherein each $R^{75}$ is independently selected from H and $-C(O)OR^{11}$, benzotriazol—1—yloxy, tetrazol—5—ylthio, or substituted tetrazol—5—ylthio, alkynyl, alkenyl or alkyl, said alkyl or alkenyl group optionally being substituted with halo, $-OR^{10}$ or $-CO_2R^{10}$;

$R^3$ and $R^4$ are the same or different and each independently represents H, any of the substituents of $R^1$ and $R^2$, or $R^3$ and $R^4$ taken together represent a saturated or unsaturated $C_5$–$C_7$ fused ring to the benzene ring (Ring III);

$R^5$, $R^6$, $R^7$ and $R^8$ each independently represents H, —$CF_3$, —$COR^{10}$, alkyl or aryl, said alkyl or aryl optionally being substituted with —$OR^{10}$, —$SR^{10}$, —$S(O)_tR^{11}$, —$NR^{10}COOR^{11}$, —$N(R^{10})_2$, —$NO_2$, —$COR^{10}$, —$OCOR^{10}$, —$OCO_2R^{11}$, —$CO_2R^{10}$, $OPO_3R^{10}$ or one of $R^5$, $R^6$, $R^7$ and $R^8$ can be taken in combination with $R^{40}$ as defined below to represent —$(CH_2)_r$—wherein r is 1 to 4 which can be substituted with alkyl, alkoxy, —$CF_3$ or aryl, or $R^5$ is combined with $R^6$ to represent =O or =S and/or $R^7$ is combined with $R^8$ to represent =O or =S;

$R^{10}$ and $R^{12}$ independently represent H, alkyl, cycloalkyl, cycloalkylalkyl, heteroaryl, aryl, aralkyl or —$NR^{40}R^{42}$ wherein $R^{40}$ and $R^{42}$ independently represent H, aryl, alkyl, aralkyl, heteroaryl, heteroarylalkyl, heterocycloalkyl, heterocycloalkylalkyl, heteroalkyl, cycloalkyl, cycloalkylalkyl, alkenyl and alkynyl;

$R^{11}$ represents alkyl or aryl;

X represents N, CH or C, such that when X is N or CH, there is a single bond to carbon atom 11 as represented by the solid line; or when X is C, there is a double bond to carbon atom 11, as represented by the solid and dotted lines;

the dotted line between carbon atoms 5 and 6 represents an optional double bond, such that when a double bond is present, A and B independently represent —$NO_2$, —$R^{10}$, halo, —$OR^{11}$, —$OCO_2R^{11}$ or —$OC(O)R^{10}$, and when no double bond is present between carbon atoms 5 and 6, A and B each independently represent $H_2$, —$(OR^{11})_2$, H and halo, dihalo, alkyl and H, $(alkyl)_2$, —H and —$OC(O)R^{10}$, H and —$OR^{10}$, oxy, aryl and H, =$NOR^{10}$ or —O—$(CH_2)_p$—O—wherein p is 2, 3 or 4; and Z represents alkyl, aryl, aralkyl, heteroalkyl, heteroaryl, heteroarylalkyl, heterocycloalkyl, heterocycloalkylalkyl, —$OR^{40}$, —$SR^{40}$, —$CR^{40}R^{42}$ or —$NR^{40}R^{42}$ wherein $R^{40}$ and $R^{42}$ are defined hereinbefore.

2. The compound of claim 1 wherein a is N, and $R^1$ is H; $R^2$, $R^3$ and $R^4$ are halo; X is CH; and $R^5$, $R^6$, $R^7$ and $R^8$ are hydrogen.

3. The compound of claim 2 wherein Z is —$NR^{40}R^{42}$.

4. The compound of claim 3 wherein $R^{40}$ is H and $R^{42}$ is heteroarylalkyl.

5. The compound of claim 4 wherein $R^{42}$ is 2-, 3- or 4-pyridylmethyl N—oxide.

6. The compound of claim 1 selected from any of the following formulae:

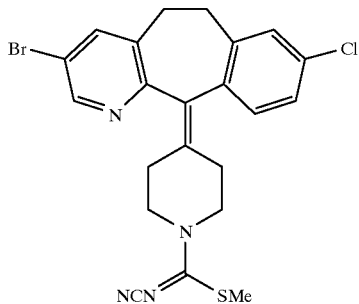

-continued

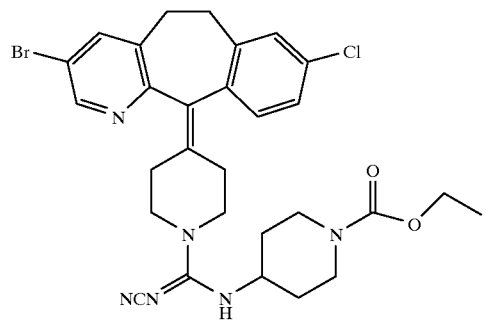

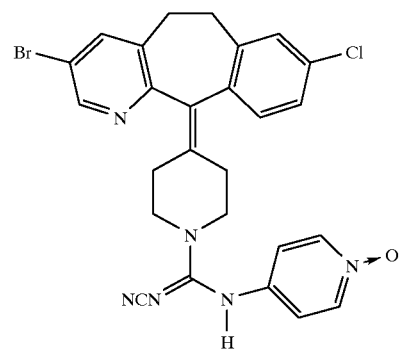

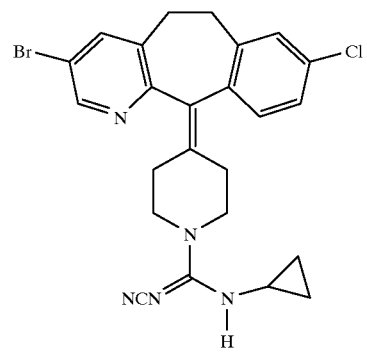

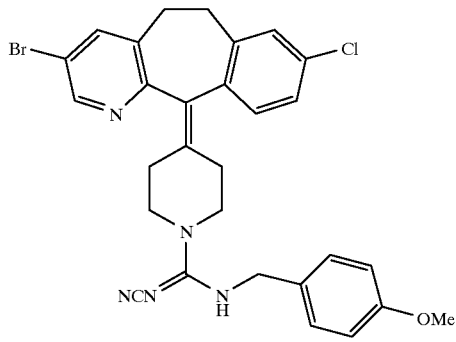

97
-continued
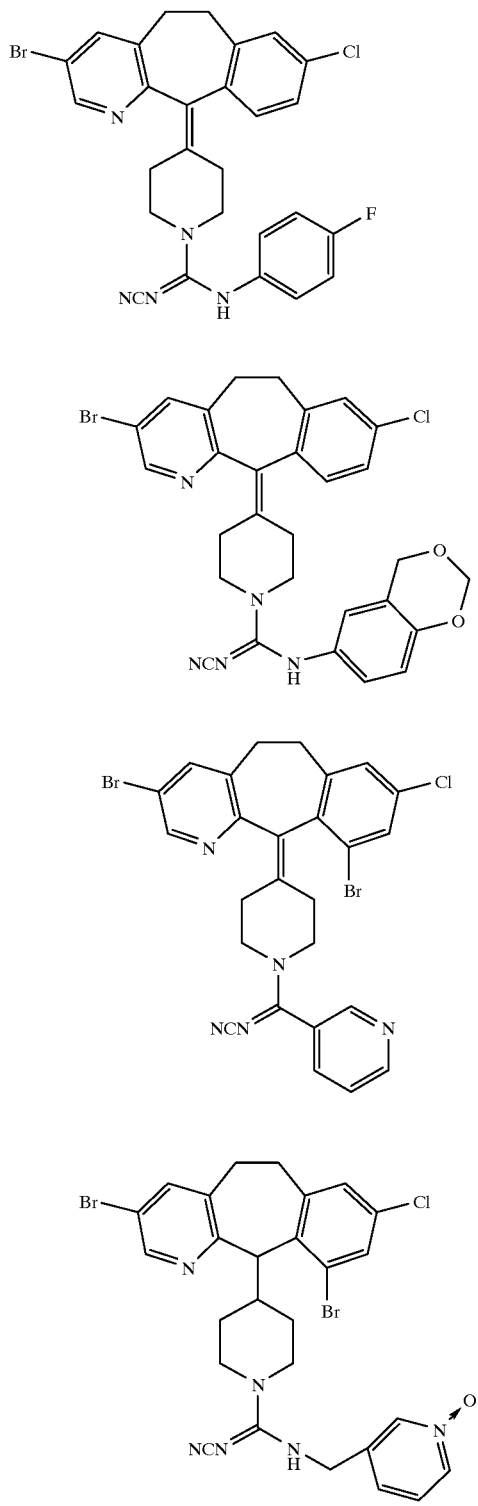
98
-continued
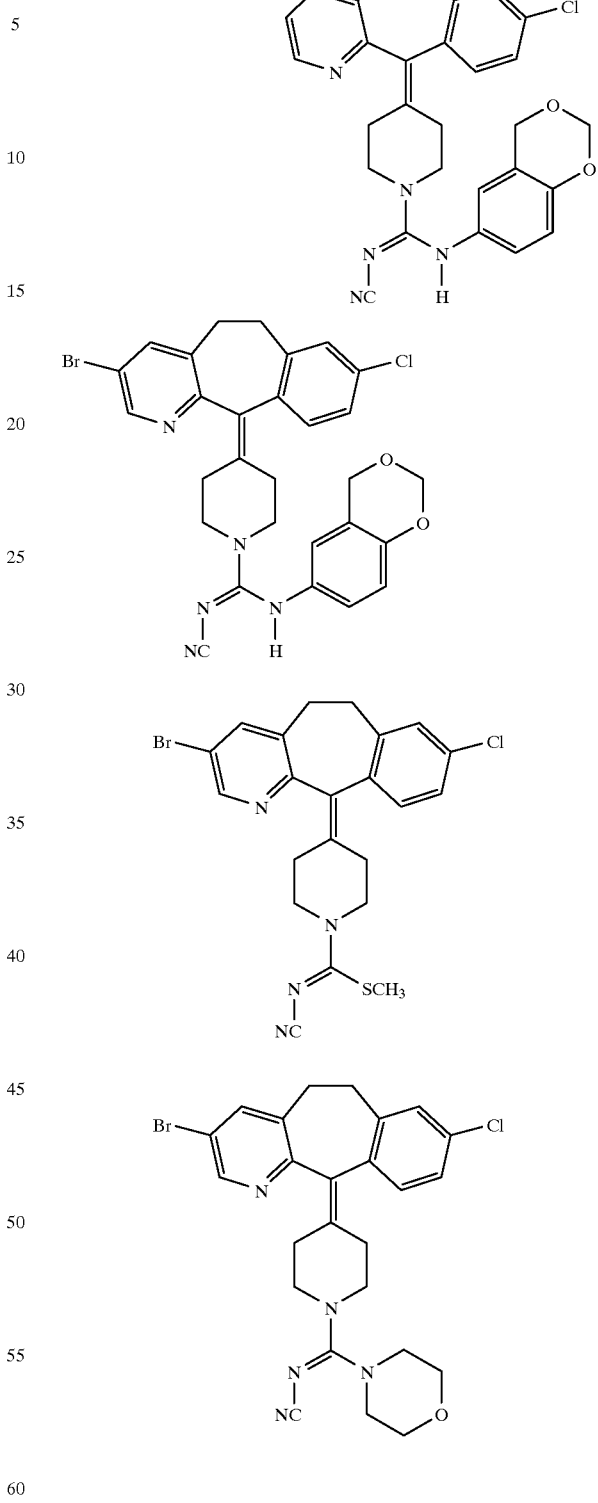

99
-continued
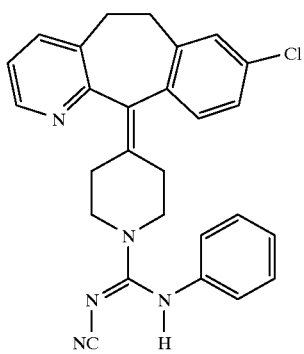
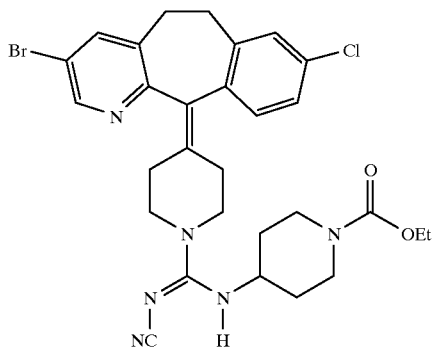
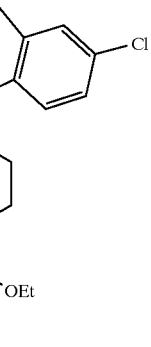
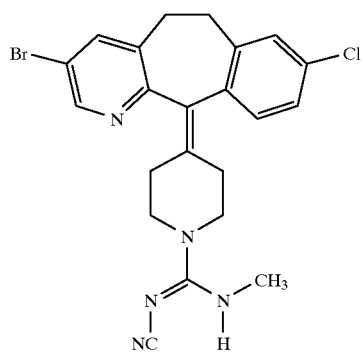
100
-continued
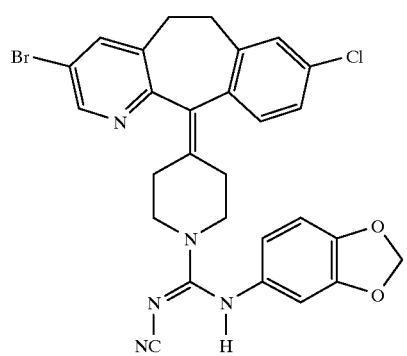
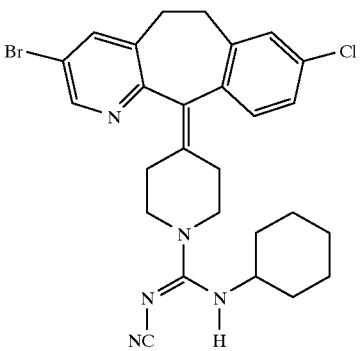
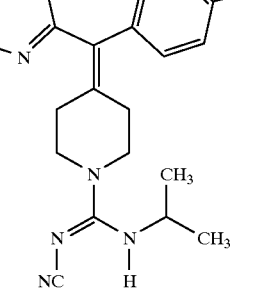

101
-continued
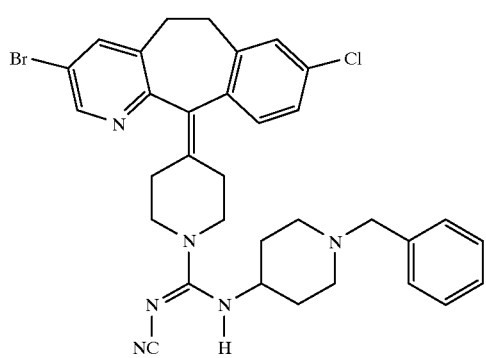
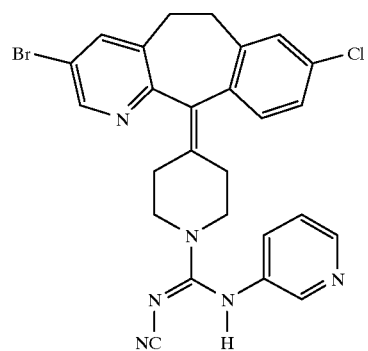
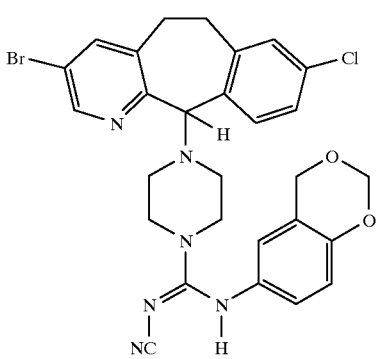
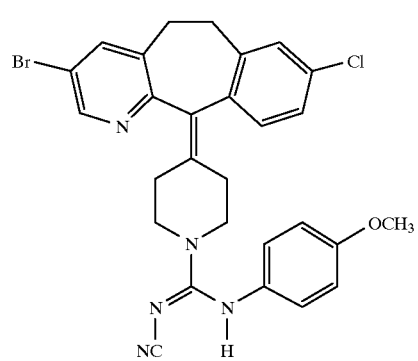
102
-continued
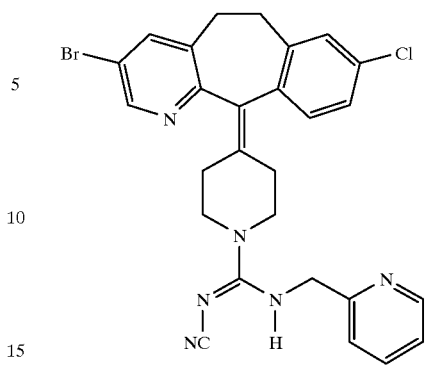
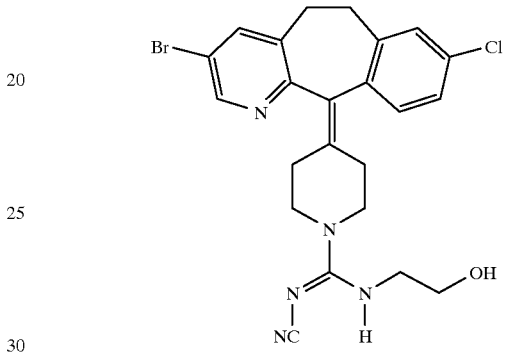
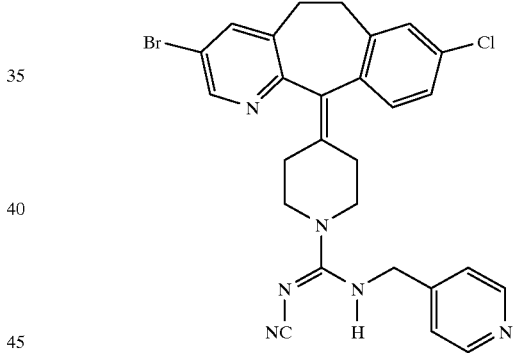
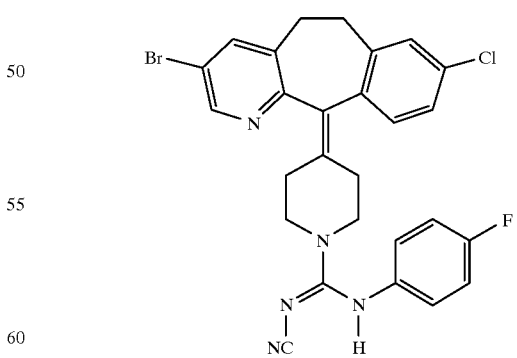

103
-continued
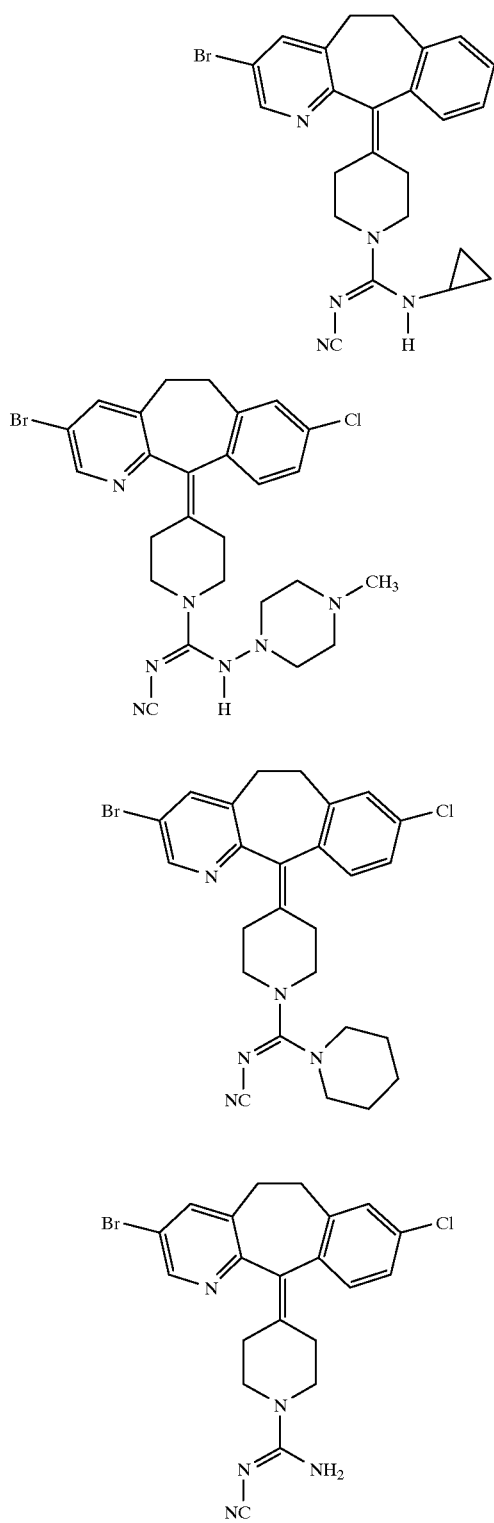
104
-continued
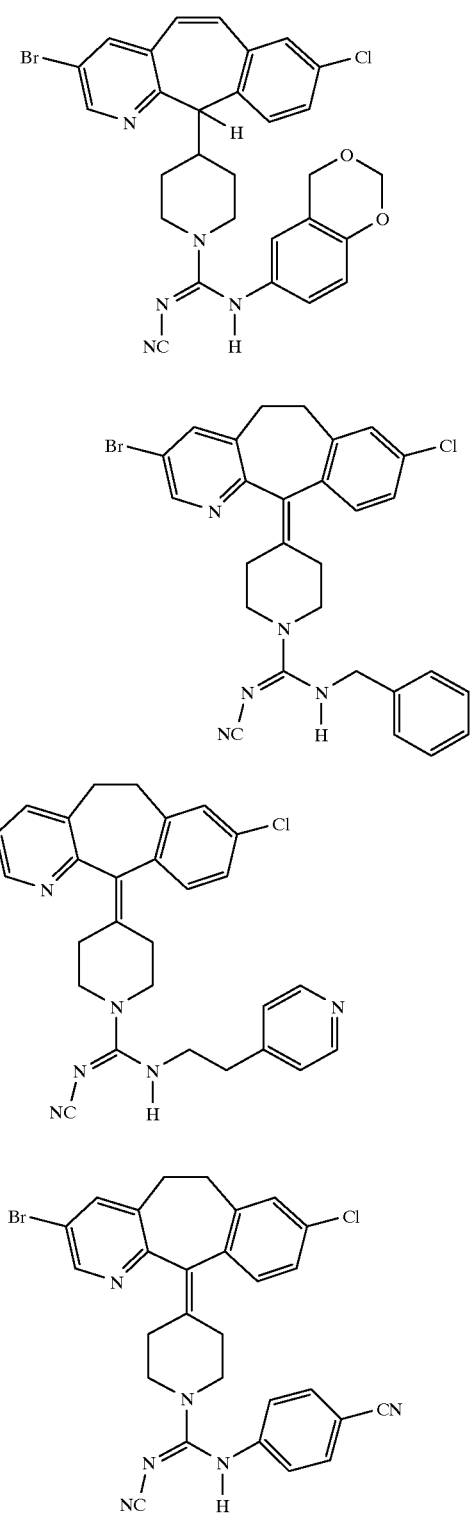

105
-continued
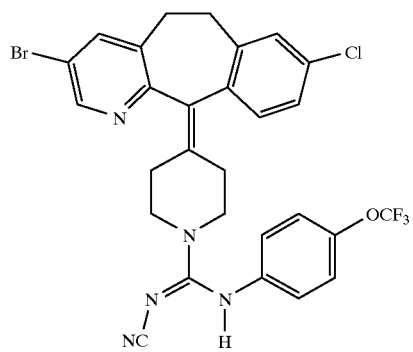
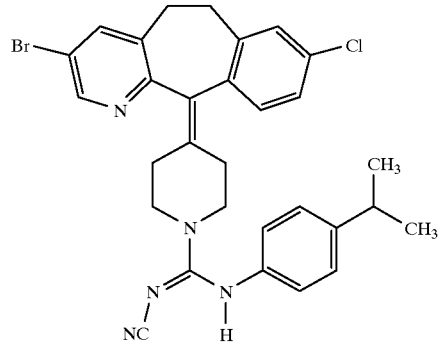
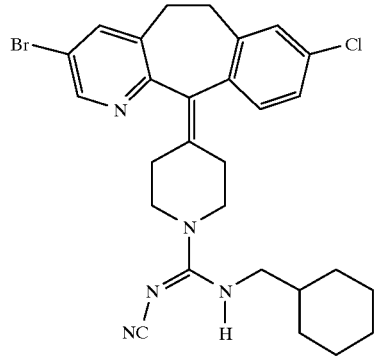
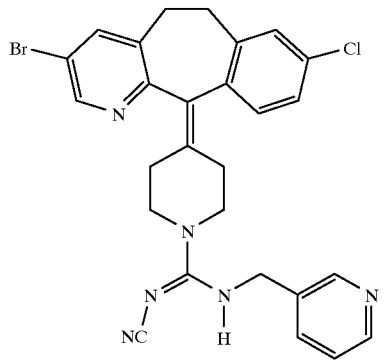
106
-continued
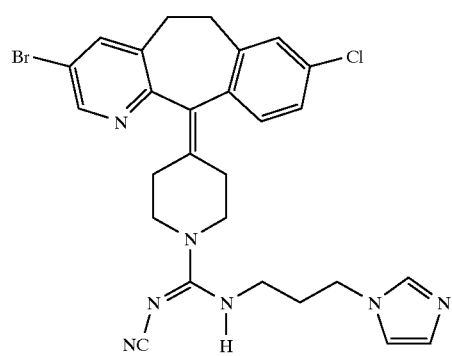
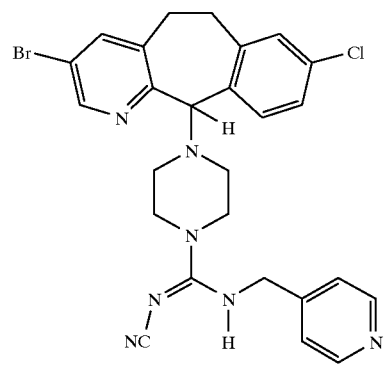
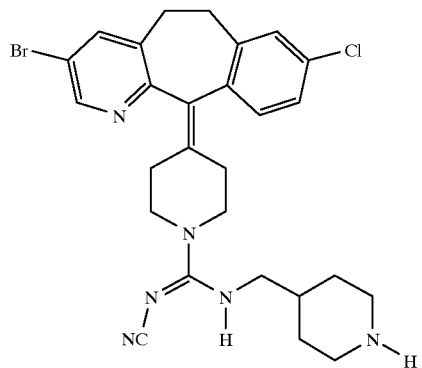
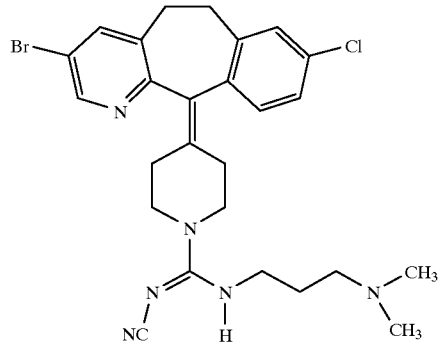

107
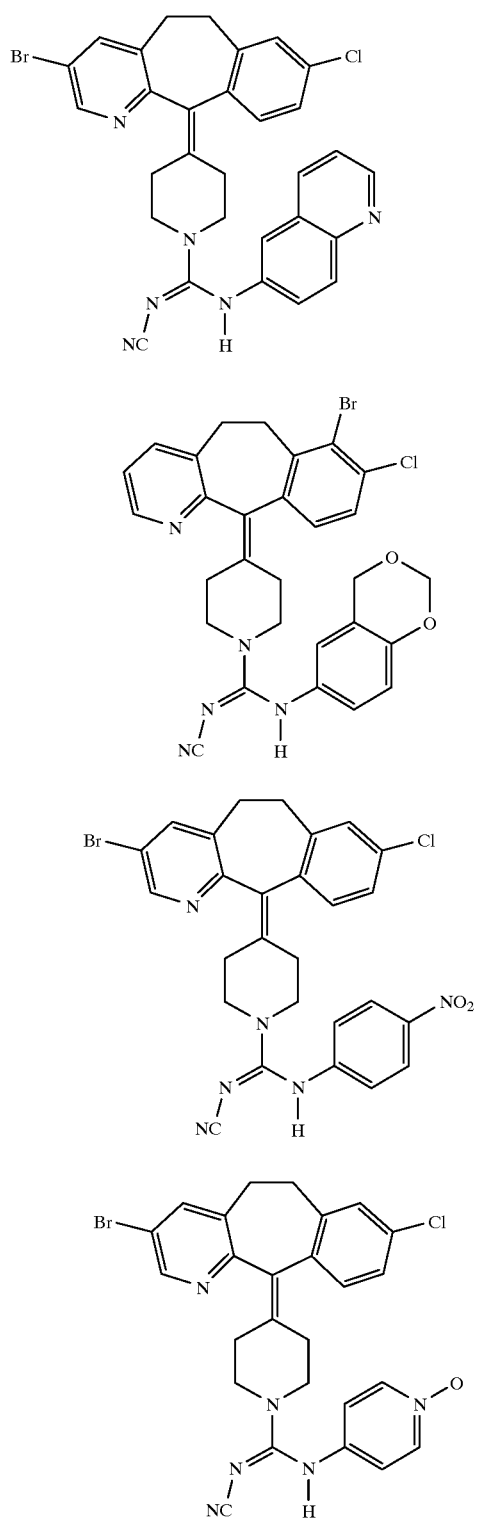
108
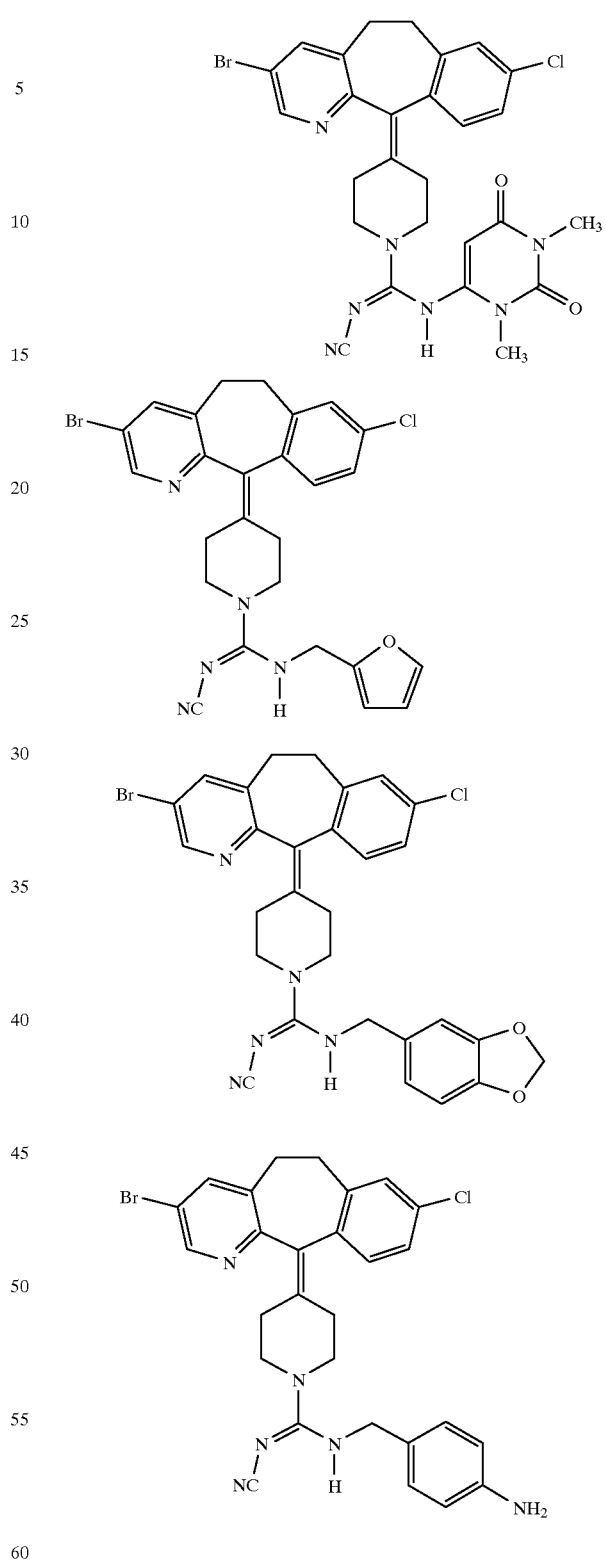

109
-continued
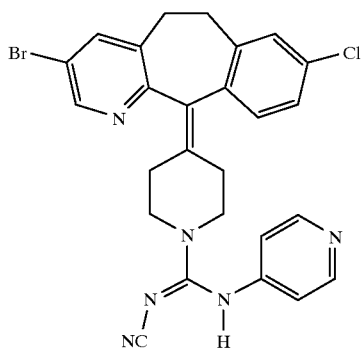
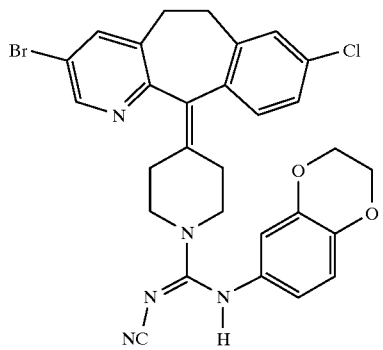
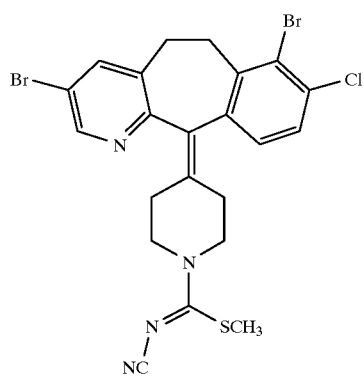
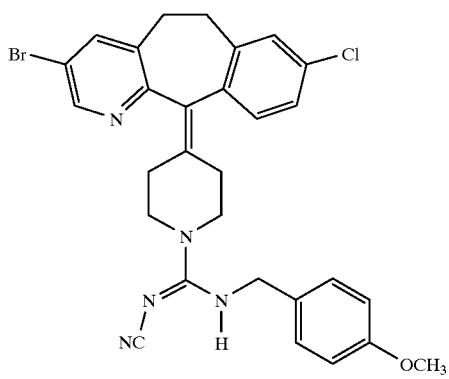
110
-continued
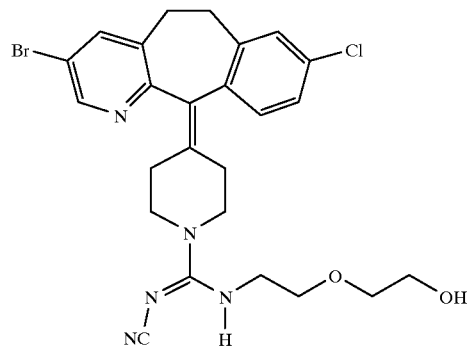
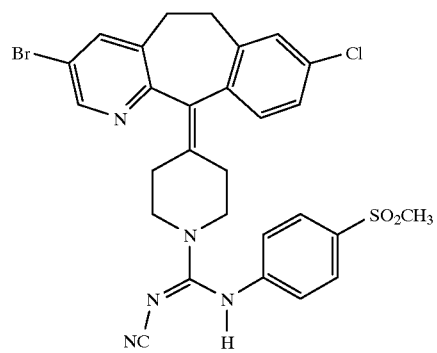
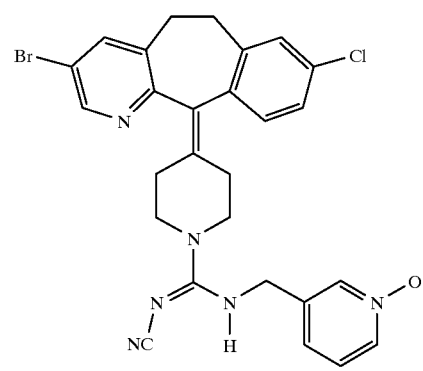

111
-continued
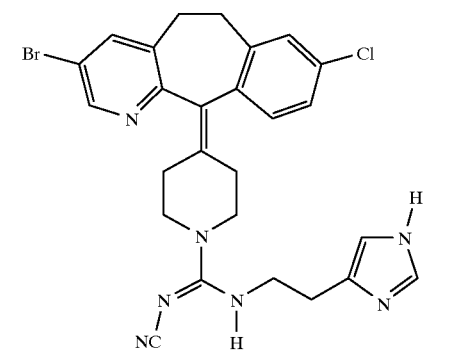
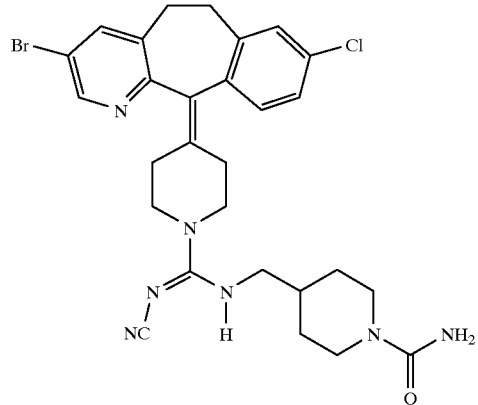
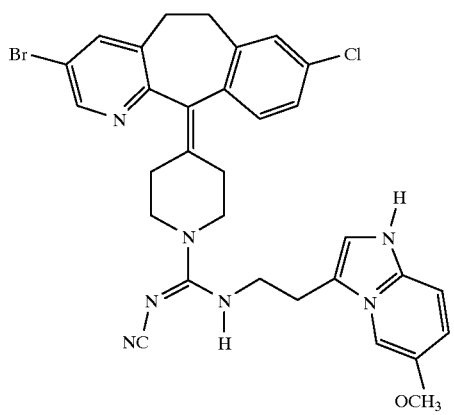
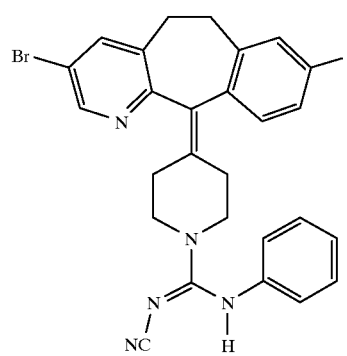
112
-continued
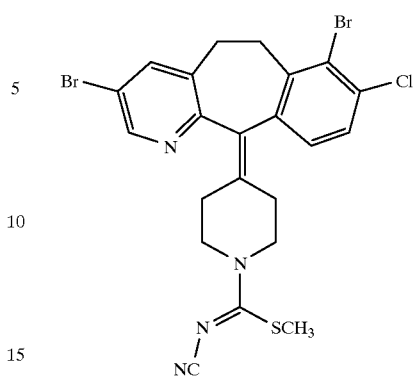
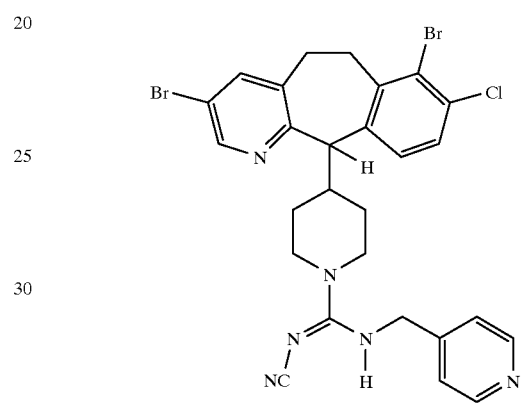
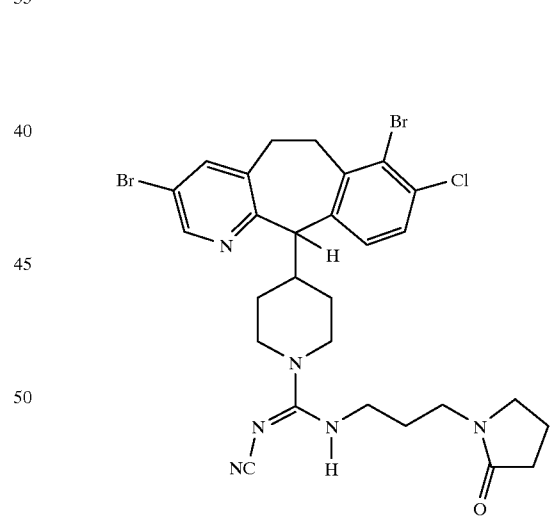

113
-continued
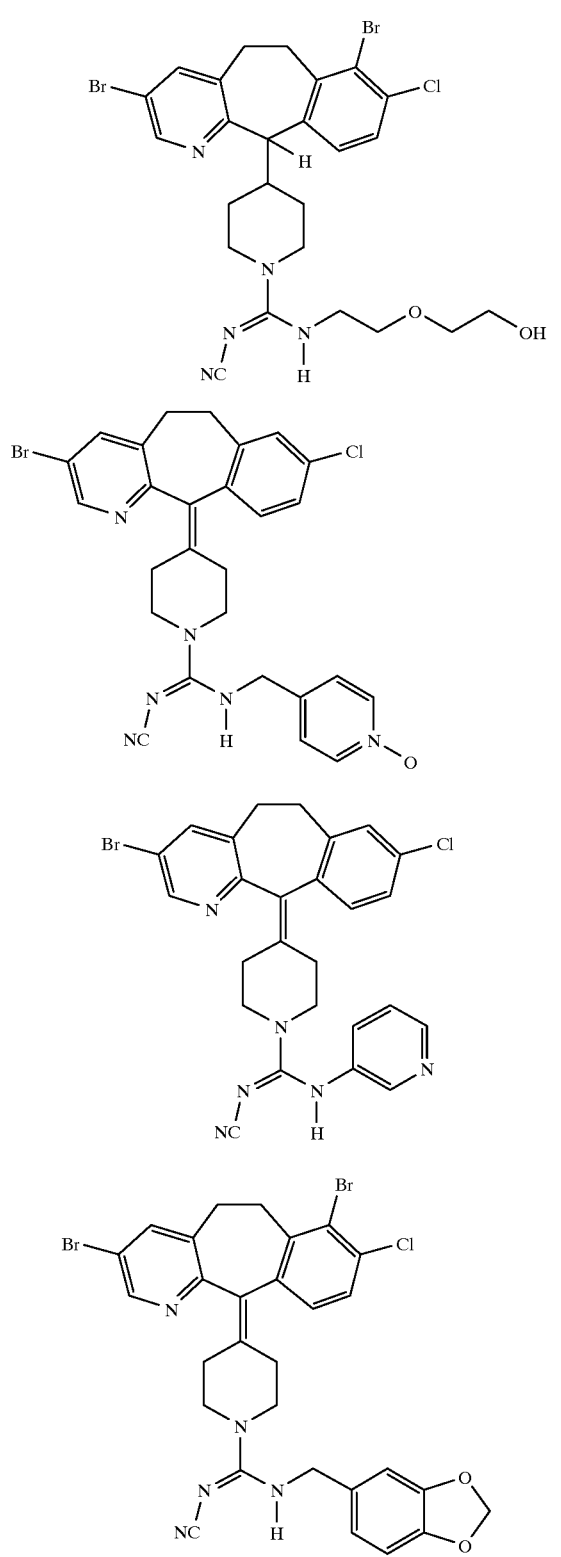
114
-continued
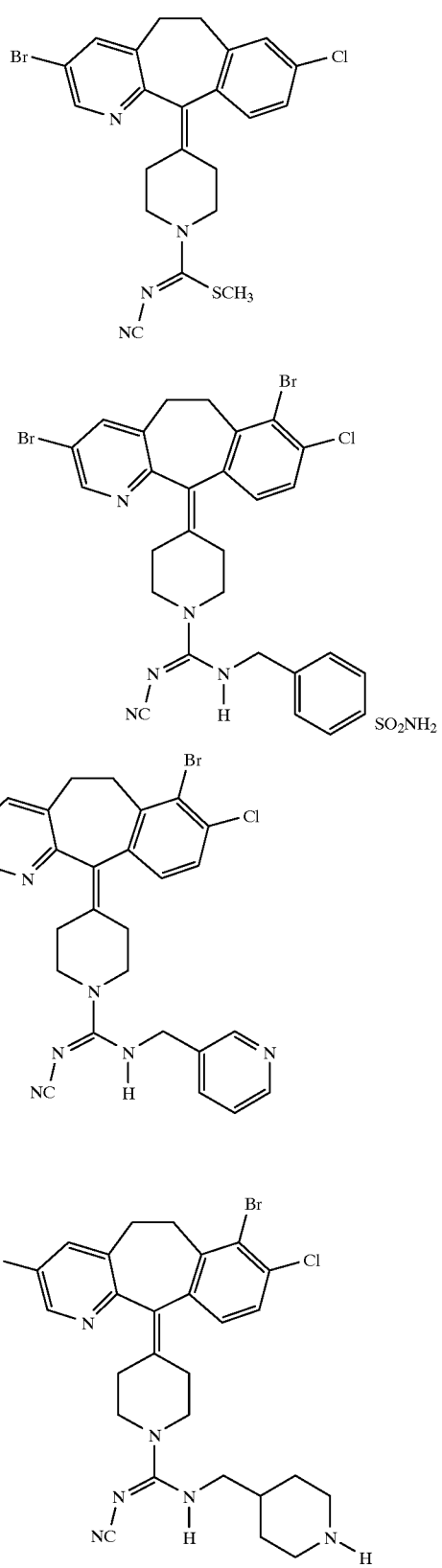

115
-continued
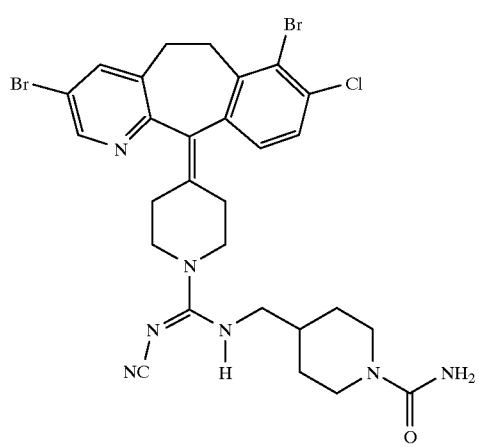
116
-continued
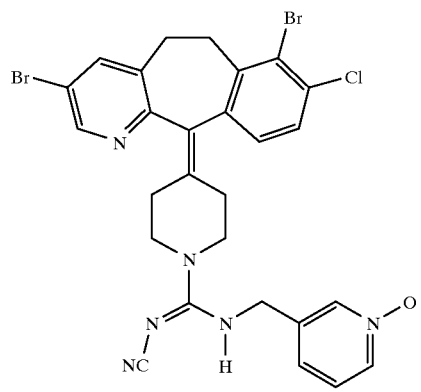
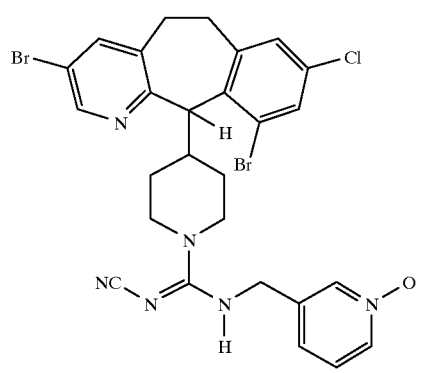
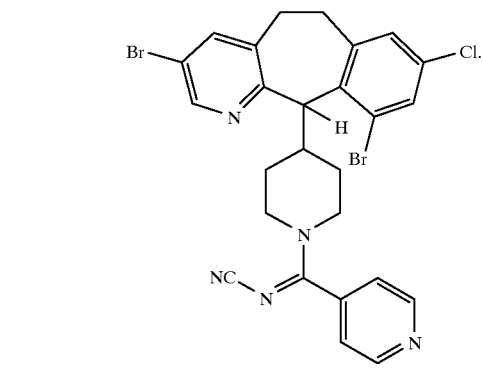
7. The compound of claim 1 of the formula:
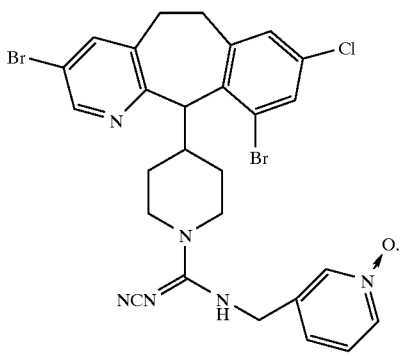

8. A pharmaceutical composition for inhibiting the abnormal growth of cells comprising an effective amount of compound of claim 1 in combination with a pharmaceutically acceptable carrier.

9. A method for inhibiting the abnormal growth of cells comprising administering an effective amount of a compound of claim 1.

10. The method of claim 9 wherein the the cells inhibited are tumor cells expressing an activated ras oncogene.

11. The method of claim 9 wherein the cells inhibited are pancreatic tumor cells, lung cancer cells, myeloid leukemia tumor cells, thyroid follicular tumor cells, myelodysplastic tumor cells, epidermal carcinoma tumor cells, bladder carcinoma tumor cells or colon tumors cells.

12. The method of claim 9 wherein the inhibition of the abnormal growth of cells occurs by the inhibition of ras farnesyl protein transferase.

13. The method of claim 9 wherein the inhibition is of tumor cells wherein the Ras protein is activated as a result of oncogenic mutation in genes other than the Ras gene.

* * * * *